US012564733B2

(12) United States Patent
Privalikhin et al.

(10) Patent No.: US 12,564,733 B2
(45) Date of Patent: Mar. 3, 2026

(54) METHODS FOR OPTIMIZING TREATMENT TIME AND PLAN QUALITY FOR RADIOTHERAPY

(71) Applicant: RefleXion Medical, Inc., Hayward, CA (US)

(72) Inventors: Aleksei Privalikhin, Sosnovy Bor (RU); Yevgen Voronenko, Sunnyvale, CA (US); Peter Demetri Olcott, Los Gatos, CA (US)

(73) Assignee: RefleXion Medical, Inc., Hayward, CA (US)

( * ) Notice: Subject to any disclaimer, the term of this patent is extended or adjusted under 35 U.S.C. 154(b) by 162 days.

(21) Appl. No.: 18/454,663

(22) Filed: Aug. 23, 2023

(65) Prior Publication Data

US 2023/0390585 A1      Dec. 7, 2023

Related U.S. Application Data

(63) Continuation of application No. PCT/US2022/017370, filed on Feb. 22, 2022.
(Continued)

(51) Int. Cl.
A61N 5/10            (2006.01)
(52) U.S. Cl.
CPC .......... A61N 5/1048 (2013.01); A61N 5/103 (2013.01); A61N 2005/1074 (2013.01)
(58) Field of Classification Search
CPC ................. A61N 5/1048; A61N 5/103; A61N 2005/1074; A61N 5/1031; G16H 40/60; G16H 20/40; G16H 50/20; G16H 50/50
See application file for complete search history.

(56) References Cited

U.S. PATENT DOCUMENTS

| | | | |
|---|---|---|---|
| 5,647,663 | A | 7/1997 | Holmes |
| 6,385,286 | B1 | 5/2002 | Fitchard et al. |

(Continued)

FOREIGN PATENT DOCUMENTS

| | | |
|---|---|---|
| CN | 101267767 A | 9/2008 |
| CN | 101489477 A | 7/2009 |

(Continued)

OTHER PUBLICATIONS

Adaptive Radiation Therapy: ISBN:9781439816356. 2011. CRC Press. X Allen Li (Ed.): 426 pages (cover only); URL: https://www.google.com/books/edition/Adaptive_Radiation_Therapy/9hEPvAlgPfMC (accessed Aug. 31, 2021).
(Continued)

*Primary Examiner* — Andrey Belousov
(74) *Attorney, Agent, or Firm* — Cooley LLP

(57)            ABSTRACT

Described herein is a graphical user interface that receives a user-specified treatment time value and displays the resultant dose distributions to a target region and/or organs-at-risk (OARs). The dose distributions are depicted as dose volume histograms (DVHs). The user-specified treatment time value may be adjusted as desired and the DVHs for the target region and/or OARs may be correspondingly updated. In some variations, the graphical user interface may comprise bounded DVHs for the target region and/or OARs, where bounds of the DVH represent the range of dose variability between a short treatment time (e.g., $T_{min}$) and a long treatment time (e.g., $T_{max}$). In some variations, the graphical user interface includes a command button that triggers fluence map optimization using the user-specified treatment time.

25 Claims, 10 Drawing Sheets

Related U.S. Application Data

(60) Provisional application No. 63/153,256, filed on Feb. 24, 2021.

(56) References Cited

U.S. PATENT DOCUMENTS

| | | | |
|---|---|---|---|
| 6,618,467 | B1 | 9/2003 | Ruchala et al. |
| 6,714,620 | B2 | 3/2004 | Caflisch et al. |
| 8,107,589 | B2 | 1/2012 | Sakurai et al. |
| 8,315,357 | B2 | 11/2012 | Zhu et al. |
| 8,605,857 | B1 | 12/2013 | Renner |
| 9,019,307 | B1 | 4/2015 | Grimm |
| 10,307,615 | B2 | 6/2019 | Ollila et al. |
| 10,456,600 | B2 | 10/2019 | Owens et al. |
| 10,674,983 | B2 | 6/2020 | Black |
| 10,918,884 | B2 | 2/2021 | O'Connor et al. |
| 11,167,153 | B2 | 11/2021 | Bokrantz et al. |
| 11,173,322 | B2 | 11/2021 | Kuusela et al. |
| 11,648,418 | B2 | 5/2023 | Owens et al. |
| 12,214,219 | B2 | 2/2025 | Owens et al. |
| 12,303,718 | B2 | 5/2025 | Owens et al. |
| 2002/0137991 | A1 | 9/2002 | Scarantino et al. |
| 2004/0079899 | A1 | 4/2004 | Ma |
| 2004/0096033 | A1 | 5/2004 | Seppi et al. |
| 2004/0122308 | A1 | 6/2004 | Ding |
| 2005/0111621 | A1 | 5/2005 | Riker et al. |
| 2005/0207531 | A1 | 9/2005 | Dempsey et al. |
| 2006/0173294 | A1 | 8/2006 | Ein-Gal |
| 2008/0226030 | A1 | 9/2008 | Otto |
| 2009/0117044 | A1 | 5/2009 | Hengerer et al. |
| 2010/0086183 | A1 | 4/2010 | Vik et al. |
| 2011/0163238 | A1 | 7/2011 | Teshigawara et al. |
| 2011/0200170 | A1 | 8/2011 | Nord et al. |
| 2011/0283235 | A1* | 11/2011 | Kling .................... G06F 1/3234 |
| | | | 715/833 |
| 2011/0291015 | A1 | 12/2011 | Mazin |
| 2012/0250971 | A1 | 10/2012 | Holmes et al. |
| 2012/0292534 | A1 | 11/2012 | Geneser et al. |
| 2012/0323599 | A1 | 12/2012 | Bal et al. |
| 2014/0005464 | A1 | 1/2014 | Bharat et al. |
| 2014/0252227 | A1 | 9/2014 | Sasai et al. |
| 2014/0270053 | A1 | 9/2014 | Larson |
| 2014/0275704 | A1 | 9/2014 | Zhang et al. |
| 2015/0161338 | A1 | 6/2015 | Scherrer et al. |
| 2015/0224342 | A1 | 8/2015 | Baltes et al. |
| 2015/0251017 | A1* | 9/2015 | De Crevoisier ..... A61N 5/1071 |
| | | | 250/252.1 |
| 2015/0360056 | A1 | 12/2015 | Xing et al. |
| 2016/0074541 | A1 | 3/2016 | Zalutsky et al. |
| 2016/0140300 | A1 | 5/2016 | Purdie et al. |
| 2016/0193480 | A1 | 7/2016 | Ribbing et al. |
| 2016/0361566 | A1 | 12/2016 | Larkin et al. |
| 2016/0361568 | A1 | 12/2016 | Chappelow et al. |
| 2017/0014642 | A1 | 1/2017 | An et al. |
| 2017/0028220 | A1 | 2/2017 | Schulte et al. |
| 2017/0095678 | A1 | 4/2017 | Oster et al. |
| 2019/0091487 | A1* | 3/2019 | Pal ....................... A61N 5/1049 |
| 2020/0197729 | A1 | 6/2020 | Owens et al. |
| 2020/0306559 | A1 | 10/2020 | Kuusela et al. |
| 2021/0101021 | A1 | 4/2021 | Fredriksson |
| 2021/0138267 | A1 | 5/2021 | Nord et al. |
| 2022/0001209 | A1 | 1/2022 | Owens et al. |
| 2022/0176156 | A1* | 6/2022 | Meijers ................ A61N 5/1043 |
| 2022/0199221 | A1 | 6/2022 | Khuntia et al. |
| 2025/0256126 | A1 | 8/2025 | Owens et al. |

FOREIGN PATENT DOCUMENTS

| | | |
|---|---|---|
| CN | 101496018 A | 7/2009 |
| CN | 102068763 A | 5/2011 |
| CN | 102641561 A | 8/2012 |
| CN | 103209736 A | 7/2013 |
| CN | 103845068 A | 6/2014 |
| CN | 104866928 A | 8/2015 |
| CN | 104994909 A | 10/2015 |
| EP | 2 072 081 A1 | 6/2009 |
| EP | 2 904 974 A1 | 8/2015 |
| EP | 2 990 078 A1 | 3/2016 |
| EP | 3 581 241 A1 | 12/2019 |
| EP | 3 264 298 A1 | 4/2020 |
| EP | 3 546 023 B1 | 1/2021 |
| JP | 2002-522128 A | 7/2002 |
| JP | 2009-160308 A | 7/2009 |
| JP | 2009-538195 A | 11/2009 |
| JP | 2012-035072 A | 2/2012 |
| JP | 2013-059576 A | 4/2013 |
| JP | 2014-023741 A | 2/2014 |
| JP | 2014-503315 A | 2/2014 |
| JP | 2016-055161 A | 4/2016 |
| JP | 2016-168077 A | 9/2016 |
| WO | WO-00/59576 A1 | 10/2000 |
| WO | WO-2008/013598 A2 | 1/2008 |
| WO | WO-2008/013598 A3 | 1/2008 |
| WO | WO-2013/024380 A1 | 2/2013 |
| WO | WO-2013/054788 A1 | 4/2013 |
| WO | WO-2013/093852 A1 | 6/2013 |
| WO | WO-2015/168431 A1 | 11/2015 |
| WO | WO-2016/001046 A1 | 1/2016 |
| WO | WO-2017/081768 A1 | 5/2017 |
| WO | WO-2019/238602 A1 | 12/2019 |
| WO | WO-2020/177844 A1 | 9/2020 |
| WO | WO-2020/234032 A1 | 11/2020 |
| WO | WO-2022/003060 A1 | 1/2022 |
| WO | WO-2024/182320 A1 | 9/2024 |

OTHER PUBLICATIONS

Chen, X. et al. (2012). "Smoothing proximal gradient method for general structured sparse regression," The Annals of Applied Statistics 6:719-752.

Croteau, E. et al. (2016)."PET Metabolic Biomarkers for Cancer," Biomark Cancer. 8(Suppl 2):61-69.

Extended European Search Report mailed on Oct. 15, 2019, for European Application No. 17 764 132.1, filed on Mar. 9, 2017, 4 pages.

Extended European Search Report mailed on Jun. 14, 2021, for EP Application No. 18 821 003.3, filed on Jun. 22, 2018, 5 pages.

Extended European Search Report mailed on Mar. 15, 2021, for EP Application No. 18 837 615.6, filed on Jul. 26, 2018, 8 pages.

Final Office Action mailed on May 18, 2022, for U.S. Appl. No. 16/016,272, filed Jun. 22, 2018, 31 pages.

Final Office Action mailed on Jul. 14, 2021, for U.S. Appl. No. 16/582,308, filed Sep. 25, 2019, 8 pages.

Final Office Action mailed on Sep. 15, 2022, for U.S. Appl. No. 16/582,308, filed Sep. 25, 2019, 10 pages.

Fredriksson (2013). "Robust optimization of radiation therapy accounting for geometric uncertainty," KTH Engin. Sciences, pp. 8-14.

Hoeben, B.A.W. et al. (2013). "Molecular PET imaging for biology-guided adaptive radiotherapy of head and neck cancer," Acta Oncologica 52:1257-1271.

International Search Report mailed on Jun. 27, 2017, for PCT Patent Application No. PCT/US2017/021647, filed on Mar. 9, 2017, 3 pages.

International Search Report mailed on Nov. 16, 2018, for PCT Application No. PCT/US2018/039104, filed on Jun. 22, 2018, 4 pages.

International Search Report mailed on Oct. 3, 2018, for PCT Application No. PCT/US2018/043954, filed on Jul. 26, 2018, 3 pages.

International Search Report mailed on May 24, 2022, for PCT Patent Application No. PCT/US2022/017370, filed on Feb. 22, 2022, 3 pages.

Kim et al. "18F-FDG PET/CT of Advanced Gastric Carcinoma and Association of H ER2 Expression with Standardized Uptake Value." Asia Oceania J Nucl Med Biol, 2014; 2(1): 12-18.

Kong et al. "Effect of Midtreatment PET/CT-Adapted Radiation Therapy with Concurrent Chemotherapy in Patients with Locally Advanced Non-Small-Cell Lung Cancer." JAMA Oncol. Oct. 2017; 3(10): 1358-1365. Published online Oct. 12, 2017. Prepublished online Jun. 1, 2017.

(56)                References Cited

OTHER PUBLICATIONS

Non-Final Office Action mailed on Jun. 26, 2020, for U.S. Appl. No. 16/122,735, filed Sep. 5, 2018, 16 pages.

Non-Final Office Action mailed on Sep. 21, 2021, for U.S. Appl. No. 16/016,272, filed Jun. 22, 2018, 34 pages.

Non-Final Office Action mailed on Feb. 11, 2021, for U.S. Appl. No. 16/582,308, filed Sep. 25, 2019, 9 pages.

Non-Final Office Action mailed on Jun. 8, 2022, for U.S. Appl. No. 16/582,308, filed Sep. 25, 2019, 9 pages.

Non-Final Office Action mailed on Nov. 21, 2022, for U.S. Appl. No. 16/016,272, filed Jun. 22, 2018, 27 pages.

Non-Final Office Action mailed on Jun. 29, 2023, for U.S. Appl. No. 17/479,873, filed Sep. 20, 2021, 10 pages.

Notice of Allowance mailed on Jul. 25, 2019, for U.S. Appl. No. 16/046,746, filed Jul. 26, 2018, 8 pages.

Notice of Allowance mailed on Aug. 15, 2019, for U.S. Appl. No. 16/046,746, filed Jul. 26, 2018, 7 pages.

Notice of Allowance mailed on Dec. 11, 2020, for U.S. Appl. No. 16/122,735, filed Sep. 5, 2018, 10 pages.

Notice of Allowance mailed on Mar. 9, 2023, for U.S. Appl. No. 16/016,272, filed Jun. 22, 2018, 8 pages.

Thorek, D. "Positron lymphography: multimodal, high-resolution, dynamic mapping and resection of lymph nodes after X intradermal injection of 18F-FDG." J Nucl Med. Sep. 2012;53(9):1438-45.

Thorwarth, D. et al. (2010). "Physical radiotherapy treatment planning based on functional PET/CT data," Radiotherapy Oncology, pp. 317-324.

Tuncel, N. "Adaptive radiotherapy from past to future frontiers." International Journal of Radiology & Radiation Therapy 2021; 8(2):81-84.

Written Opinion of the International Searching Authority mailed on Jun. 27, 2017, for PCT Patent Application No. PCT/US2017/021647, filed on Mar. 9, 2017, 5 pages.

Written Opinion of the International Searching Authority mailed on Nov. 16, 2018, for PCT Application No. PCT/US2018/039104, filed on Jun. 22, 2018, 6 pages.

Written Opinion of the International Searching Authority mailed on Oct. 3, 2018, for PCT Application No. PCT/US2018/043954, filed on Jul. 26, 2018, 5 pages.

Written Opinion of the International Searching Authority mailed on May 24, 2022, for PCT Patent Application No. PCT/US2022/017370, filed on Feb. 22, 2022, 9 pages.

Yan, D. et al. (1997). "Adaptive radiation therapy," *Physics Med. Biol.* 42:123-132.

Zhang, H. et al. (2002). Progress in the Physics of Tumor Radiation Therapy, Beijing Medical University, China Union Medical University Joint Press, p. 164 (with English translation).

Zhao, H. et al. (2015). Practical Imaging Diagnosis, University Press, Aug. 2015, p. 167 (with English translation).

Extended European Search Report mailed on May 31, 2024, for EP Application No. 23 211 269.8, filed on Jun. 22, 2018, 5 pages.

Final Office Action mailed on Oct. 4, 2023, for U.S. Appl. No. 17/479,873, filed Sep. 20, 2021, 10 pages.

Final Office Action mailed on Jul. 8, 2024, for U.S. Appl. No. 17/479,873, filed Sep. 20, 2021, 11 pages.

Geets, X. et al. (Oct. 2007). "Adaptive biological image-guided IMRT with anatomic and functional imaging in pharyngo-laryngeal tumors: impact on target vol. delineation and dose distribution using helical tomotherapy," Radiother. Oncol. 85(1):105-115.

Guohua, H. et al. (Nov. 2002). "Chapter 8: Radionuclide diagnosis and treatment," in Bladder Tumor, Shanghai: Tongji University Press, first edition, first printing, p. 41 (with English Translation).

Hongsheng, S. (Aug. 2015). "Chapter 8: Nuclear medicine imaging," in Practical Imaging Diagnosis, Xi'an Jiaotong University Press, first edition, first printing, p. 167 (with English Translation).

International Search Report mailed on Jun. 10, 2024, for PCT Patent Application No. PCT/US2024/017358, filed on Feb. 26, 2024, 4 pages.

Non-Final Office Action mailed on Mar. 5, 2024, for U.S. Appl. No. 17/479,873, filed Sep. 20, 2021, 11 pages.

Non-Final Office Action mailed on Jun. 24, 2024, for U.S. Appl. No. 18/295,448, filed Apr. 4, 2023, 8 pages.

Notice of Allowance mailed on Sep. 29, 2024, for U.S. Appl. No. 18/295,448, filed Apr. 4, 2023, 5 pages.

Notice of Allowance mailed on Jan. 15, 2025, for U.S. Appl. No. 17/479,873, filed Sep. 20, 2021, 9 pages.

Notice of Allowance mailed on Feb. 19, 2025, for U.S. Appl. No. 17/479,873, filed Sep. 20, 2021, 5 pages.

Peng, C. et al. (Jun. 2016). "Chapter 15: Clinical radiotherapy technique," in Clinical Diagnosis and Treatment of Oncological Diseases, published by Jilin Science and Technology Press, first edition, first printing, p. 276 (with English translation).

Rocha, H. et al. (Jun. 20, 2011). "Influence of sampling in radiation therapy treatment design," 18th International Conference, Austin, TX, USA, Sep. 24-27, 2015, pp. 215-230.

Shiying, Y. (Jul. 2009). "Chapter 4: Design of radiotherapy plan," in Guidelines for Standardized Diagnosis and Treatment of Tumors, published by Huazhong University of Science and Technology Press, first edition, first printing, p. 106 (with English translation).

Written Opinion of the International Searching Authority mailed on Jun. 10, 2024, for PCT Patent Application No. PCT/US2024/017358, filed on Feb. 26, 2024, 10 pages.

Xuening, Z. (Dec. 2010). "Chapter 2: Principles and Stereotactic Techniques of LEKSELL Gamma Knife," in Gamma Knife Surgery for Intracranial Disease—Clinical Imaging, published by Tianjin Science and Technology Press, first edition, first printing, pp. 29-30 (with English Translation).

Zhiliao, Z. et al. (Mar. 2002). "Progress in Physics of Tumor Radiotherapy," Beijing Medical University and China Union Medical University Joint Publishing House, first edition, first printing, pp. 163-164 (with English translation).

* cited by examiner

<u>140</u>

| | |
|---|---|
| Receive selection of a treatment time within a range of treatment times via an input on the treatment time selector | 142 |

| | |
|---|---|
| Update the dose graphics(s) to one or more target regions and/or one or more OARs according to the selected treatment time | 144 |

| | |
|---|---|
| Output the updated dose graphics(s) to one or more target regions and/or one or more OARs to a display device | 146 |

| | |
|---|---|
| Receive a command input to initiate fluence map optimization using a cost function comprising a treatment time penalty function that incorporates the selected treatment time value | 148 |

| | |
|---|---|
| Update the dose graphic(s) to one or more target regions and/or one or more OARs according to the generated fluence map | 150 |

| | |
|---|---|
| Output the updated dose graphic(s) to one or more target regions and/or one or more OARs and the corresponding treatment time to the display device | 152 |

FIG. 1H

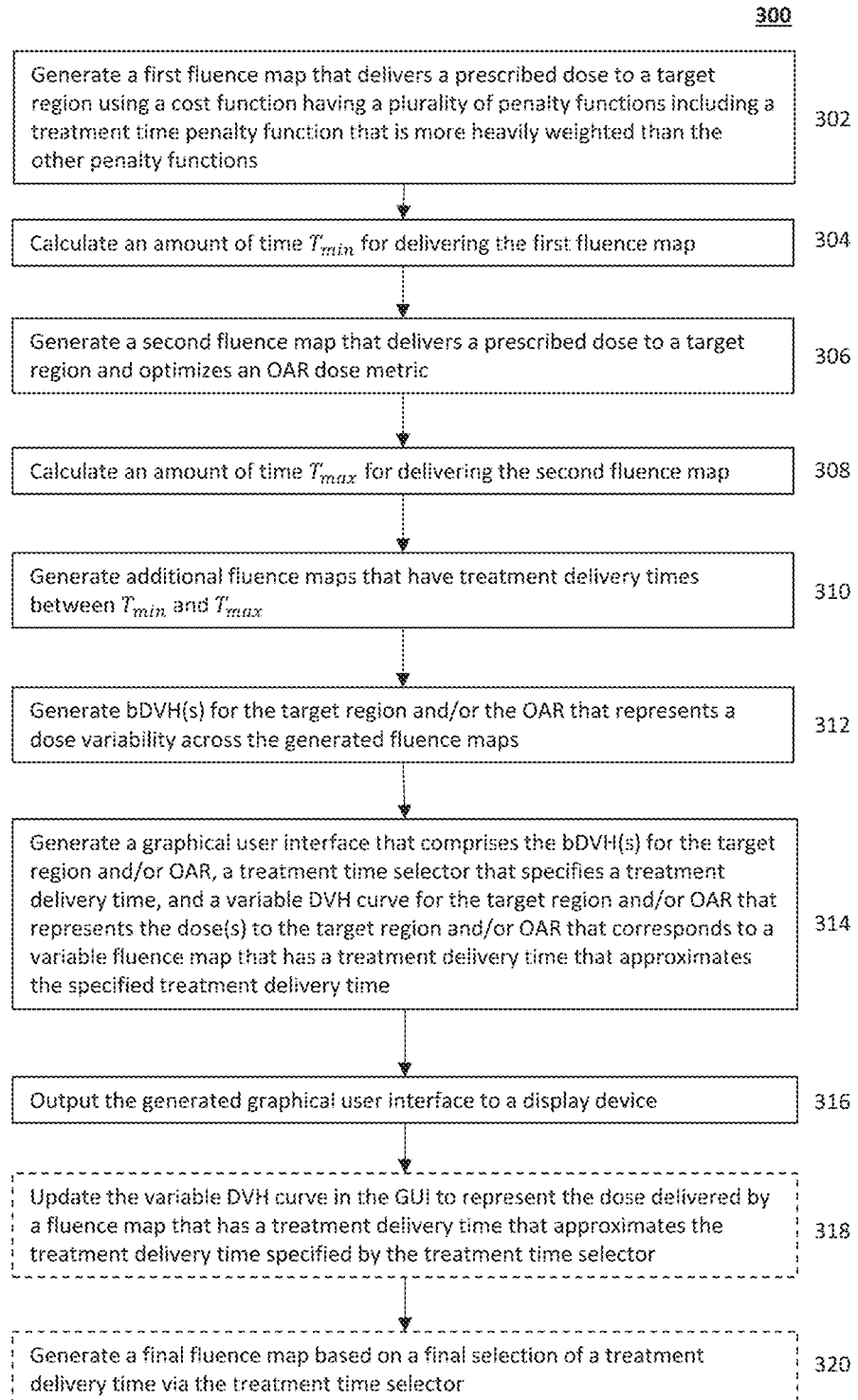

Generate a first fluence map that delivers a prescribed dose to a target region using a cost function having a plurality of penalty functions including a treatment time penalty function that is more heavily weighted than the other penalty functions — 302

Calculate an amount of time $T_{min}$ for delivering the first fluence map — 304

Generate a second fluence map that delivers a prescribed dose to a target region and optimizes an OAR dose metric — 306

Calculate an amount of time $T_{max}$ for delivering the second fluence map — 308

Generate additional fluence maps that have treatment delivery times between $T_{min}$ and $T_{max}$ — 310

Generate bDVH(s) for the target region and/or the OAR that represents a dose variability across the generated fluence maps — 312

Generate a graphical user interface that comprises the bDVH(s) for the target region and/or OAR, a treatment time selector that specifies a treatment delivery time, and a variable DVH curve for the target region and/or OAR that represents the dose(s) to the target region and/or OAR that corresponds to a variable fluence map that has a treatment delivery time that approximates the specified treatment delivery time — 314

Output the generated graphical user interface to a display device — 316

Update the variable DVH curve in the GUI to represent the dose delivered by a fluence map that has a treatment delivery time that approximates the treatment delivery time specified by the treatment time selector — 318

Generate a final fluence map based on a final selection of a treatment delivery time via the treatment time selector — 320

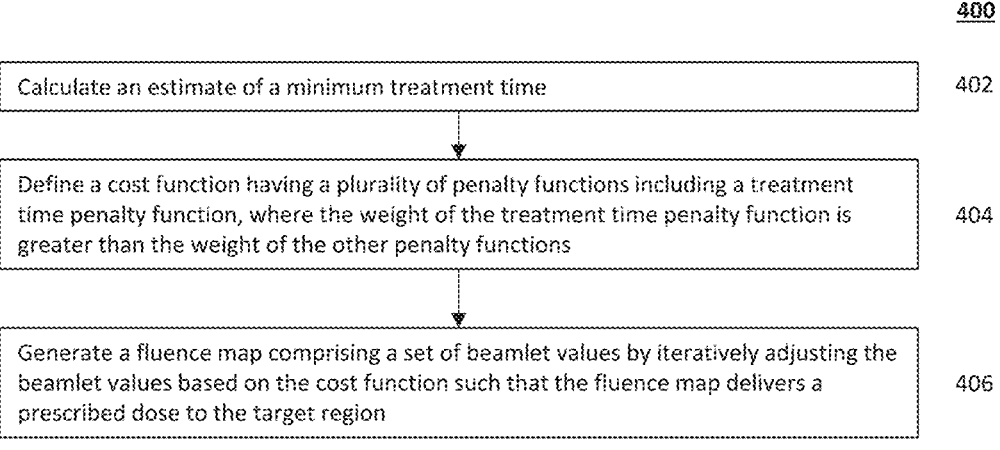

| | |
|---|---|
| Calculate an estimate of a minimum treatment time | 402 |
| Define a cost function having a plurality of penalty functions including a treatment time penalty function, where the weight of the treatment time penalty function is greater than the weight of the other penalty functions | 404 |
| Generate a fluence map comprising a set of beamlet values by iteratively adjusting the beamlet values based on the cost function such that the fluence map delivers a prescribed dose to the target region | 406 |

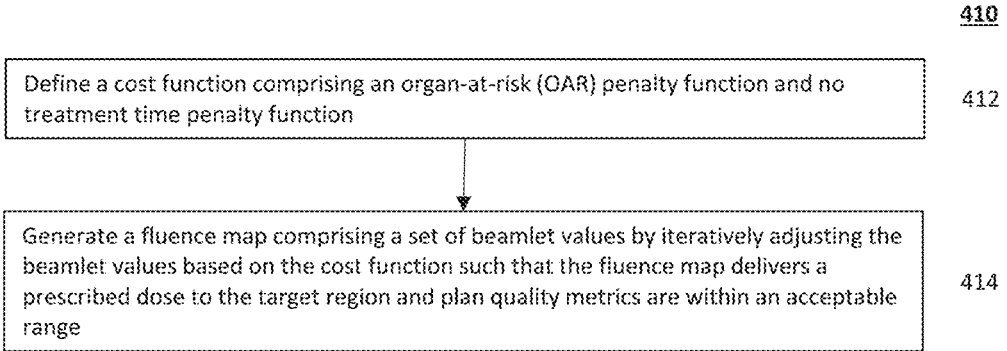

| | |
|---|---|
| Define a cost function comprising an organ-at-risk (OAR) penalty function and no treatment time penalty function | 412 |
| Generate a fluence map comprising a set of beamlet values by iteratively adjusting the beamlet values based on the cost function such that the fluence map delivers a prescribed dose to the target region and plan quality metrics are within an acceptable range | 414 |

FIG. 4B

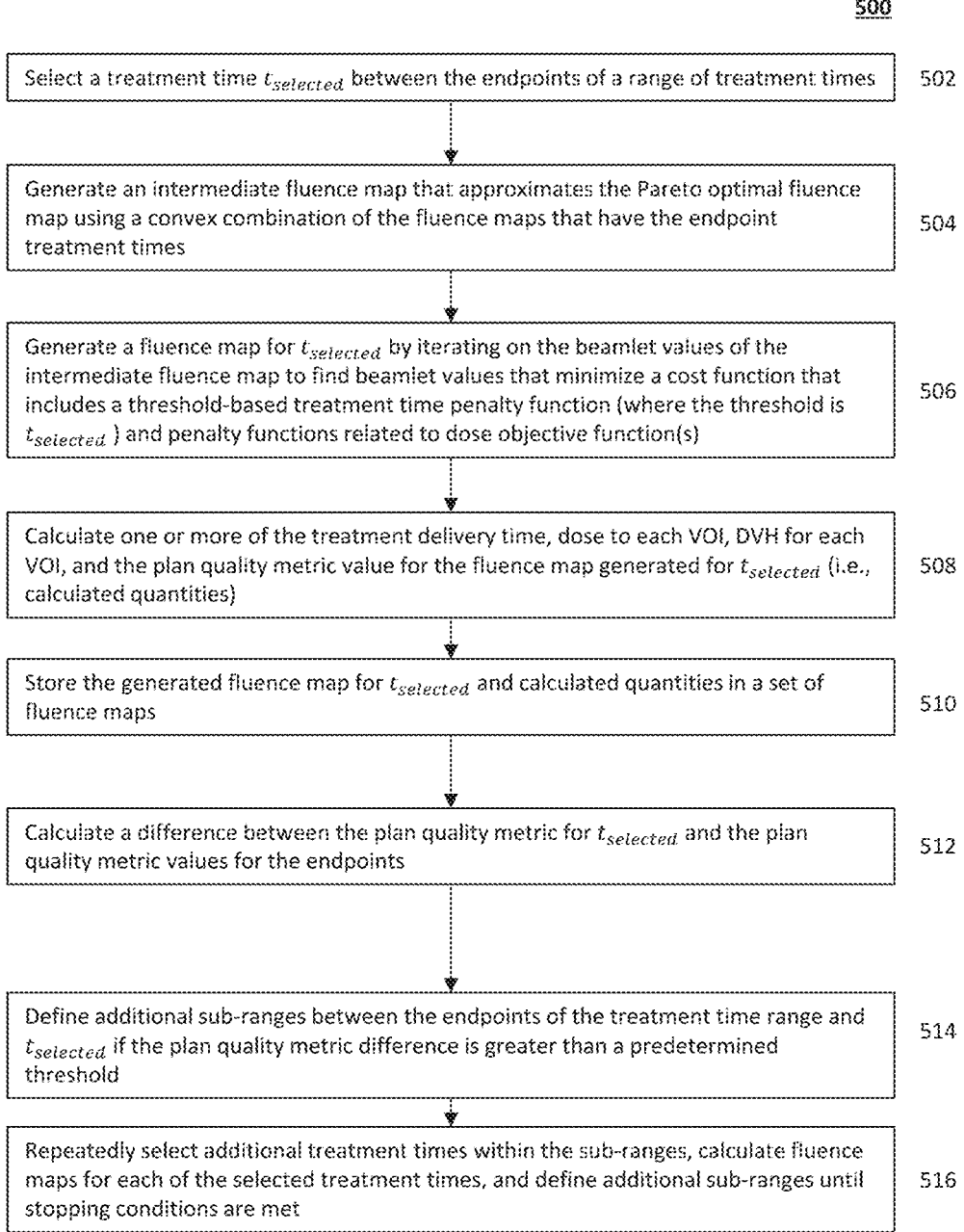

500

Select a treatment time $t_{selected}$ between the endpoints of a range of treatment times    502

Generate an intermediate fluence map that approximates the Pareto optimal fluence map using a convex combination of the fluence maps that have the endpoint treatment times    504

Generate a fluence map for $t_{selected}$ by iterating on the beamlet values of the intermediate fluence map to find beamlet values that minimize a cost function that includes a threshold-based treatment time penalty function (where the threshold is $t_{selected}$ ) and penalty functions related to dose objective function(s)    506

Calculate one or more of the treatment delivery time, dose to each VOI, DVH for each VOI, and the plan quality metric value for the fluence map generated for $t_{selected}$ (i.e., calculated quantities)    508

Store the generated fluence map for $t_{selected}$ and calculated quantities in a set of fluence maps    510

Calculate a difference between the plan quality metric for $t_{selected}$ and the plan quality metric values for the endpoints    512

Define additional sub-ranges between the endpoints of the treatment time range and $t_{selected}$ if the plan quality metric difference is greater than a predetermined threshold    514

Repeatedly select additional treatment times within the sub-ranges, calculate fluence maps for each of the selected treatment times, and define additional sub-ranges until stopping conditions are met    516

FIG. 5

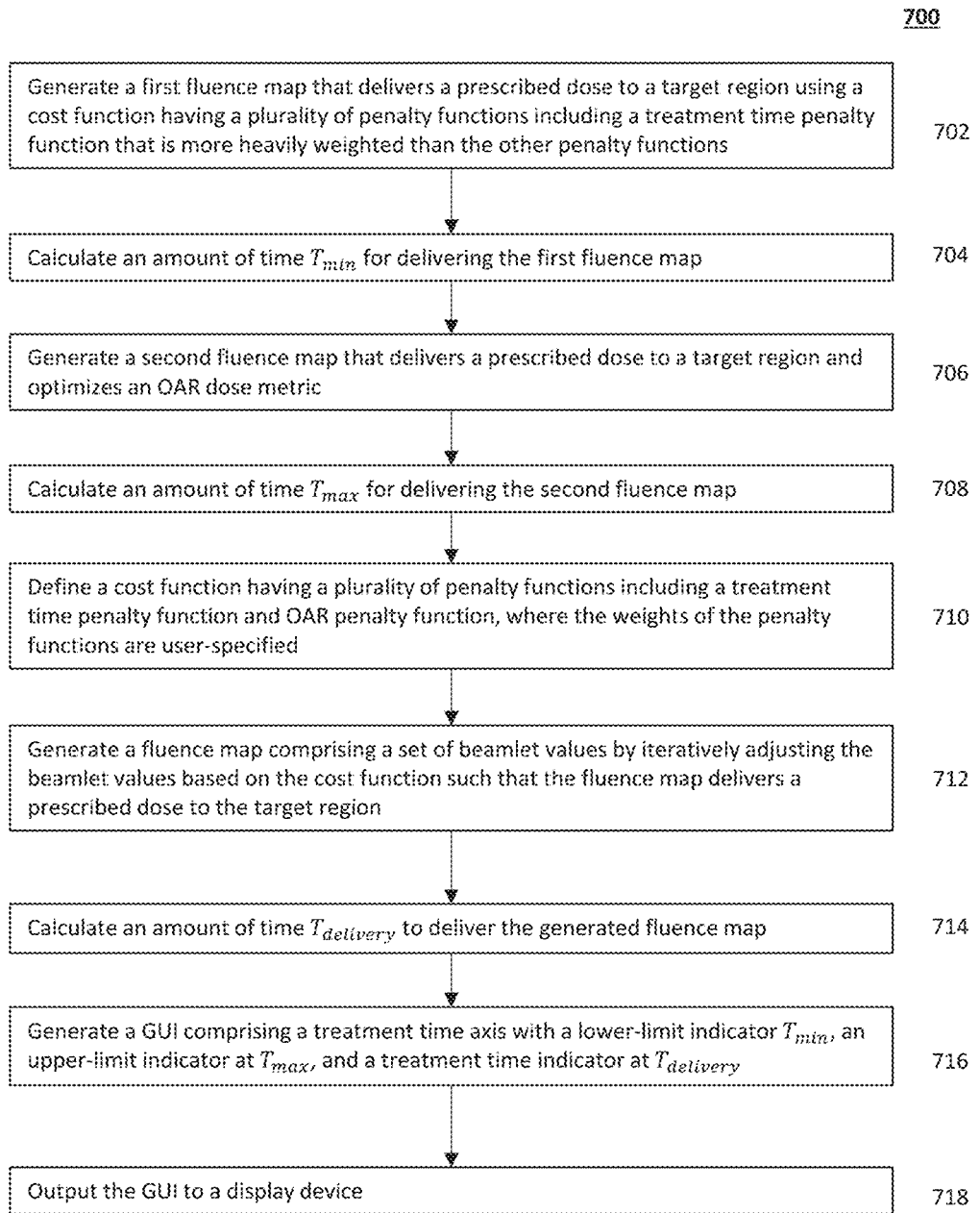

700

Generate a first fluence map that delivers a prescribed dose to a target region using a cost function having a plurality of penalty functions including a treatment time penalty function that is more heavily weighted than the other penalty functions          702

Calculate an amount of time $T_{min}$ for delivering the first fluence map          704

Generate a second fluence map that delivers a prescribed dose to a target region and optimizes an OAR dose metric          706

Calculate an amount of time $T_{max}$ for delivering the second fluence map          708

Define a cost function having a plurality of penalty functions including a treatment time penalty function and OAR penalty function, where the weights of the penalty functions are user-specified          710

Generate a fluence map comprising a set of beamlet values by iteratively adjusting the beamlet values based on the cost function such that the fluence map delivers a prescribed dose to the target region          712

Calculate an amount of time $T_{delivery}$ to deliver the generated fluence map          714

Generate a GUI comprising a treatment time axis with a lower-limit indicator $T_{min}$, an upper-limit indicator at $T_{max}$, and a treatment time indicator at $T_{delivery}$          716

Output the GUI to a display device          718

FIG. 7

METHODS FOR OPTIMIZING TREATMENT TIME AND PLAN QUALITY FOR RADIOTHERAPY

CROSS-REFERENCE TO RELATED APPLICATIONS

This application is a continuation of International Application No. PCT/US2022/017370, filed Feb. 22, 2022, which claims priority to U.S. Provisional Patent Application No. 63/153,256 filed Feb. 24, 2021, the disclosure of which is hereby incorporated by reference in its entirety.

BACKGROUND

Treatment planning for radiotherapy involves defining a radiation fluence map that delivers the prescribed dose to tumors while limiting the irradiation of surrounding healthy tissue. A treatment plan fluence map contains a plurality of radiation beamlets that, when emitted by radiotherapy system, will deliver the prescribed dose to tumors. Due to the limitations of external beam radiotherapy systems and the variable shapes, sizes, and locations of tumors, delivering a prescribed dose to a tumor invariably exposes surrounding tissue to some level of radiation. Various system and/or dose limitations as well as treatment objectives may be represented as constraints and objectives, some of which may be translated into a cost function. A cost function, which comprises a plurality of penalty functions, is defined during treatment planning to guide the optimization and generation of the fluence map so that the irradiation of non-tumor tissue is kept below a selected threshold. For example, cost functions may comprise one or more penalty functions that "discourage" excessive radiation dose to organs-at-risk (OARs), and/or one or more penalty functions that "discourage" abrupt fluence changes and/or the emission of an excessive amount of radiation by the therapeutic radiation source (e.g., total radiation emitted by a therapeutic radiation source, in monitor units).

The penalty functions of a cost function may be weighted relative to each other, where their relative weights may correspond with their relative priorities. For example, a penalty function that limits dose to the spinal cord may have a higher weight than a penalty function that reduces the number of multi-leaf collimator (MLC) leaf transitions. In many cases, the penalty function weights are defined by the user (e.g., clinician), and may be adjusted during treatment planning. However, depending on the complexity of the cost function and the patient's disease state, it may be difficult to understand the effect of a particular combination of penalty function weights on the generated fluence map and/or the resultant dose distribution to the tumor and/or OARs (collectively, the volumes of interest or VOIs). More generally, it can be challenging to understand the effect of treatment planning constraints and/or objections on the dose distribution. Accordingly, improved methods to aid a user during treatment planning are desired.

SUMMARY

Described herein is a graphical user interface that comprises a treatment time selector that is configured to receive user input that specifies a treatment time, a dose distribution plot for a VOI (e.g., a target region, an OAR, any contoured volume) that depicts a range of dose distributions for a range of treatment times, and a variable dose distribution plot that represents the dose distribution for the VOI at the specified treatment time. In one variation, the graphical user interface may comprise a bounded volume histogram (bDVH) for a VOI, where the lower and the upper bounds of the bDVH represent the range of dose distributions over a range of treatment times between $T_{min}$ and $T_{max}$, a treatment time selector configured to receive user input that specifies a treatment time within the range of treatment times, and a variable DVH that represents the dose distribution to the VOI for the specified treatment time. The variable dose distribution plot (e.g., DVH) may be updated as the user adjusts the treatment time. In some variations, the variable dose distribution plot may be dynamically updated in response to user-selection of different treatment times. For example, the variable dose distribution plot may be updated without reoptimizing the fluence map. The VOI may be a target region such as a tumor or a radiation-avoidance region such as an OAR. Some variations of the graphical user interface may comprise bDVH plots and variable DVH plots for multiple VOIs, including any combination or number of target regions and/or radiation-avoidance regions.

Also described herein are methods for generating a graphical user interface that comprises a dose distribution plot for a VOI (e.g., a target region, an OAR) that depicts a range of dose distributions for a range of treatment times and dynamically updates dose distribution plots (e.g., DVH) for one or more VOI when a user selects a different treatment time within the range of treatment times (i.e., $T_{min} \leq t_{selected} \leq T_{max}$). One variation of a method for generating a graphical user interface that depicts a range of dose distributions for a range of treatment times comprises calculating a minimum treatment time $T_{min}$ to deliver a prescribed dose to one or more VOIs, calculating a maximum treatment time $T_{max}$ to deliver a prescribed dose to one or more VOIs, generating fluence maps and/or DVHs for the one or more VOIs at the minimum treatment time $T_{min}$, the maximum treatment time $T_{max}$, and a selection of treatment times between the minimum treatment time $T_{min}$ and the maximum treatment time $T_{max}$, and generating a bDVH having upper and lower bounds that may be calculated from the generated fluence maps and/or DVHs. One variation of a method for dynamically updating dose distribution plots according to a selected treatment time may comprise interpolating between the fluence maps and/or DVHs that were generated for the selection of treatment times and generating a DVH based on the interpolation. The method may comprise generating a DVH for the selected treatment time by linearly interpolating between the DVH that corresponds to the treatment time that is less than the selected time and the DVH that corresponds to the treatment time that is greater than the selected time.

One variation of a GUI for radiotherapy planning may comprise a bounded dose volume histogram (bDVH) for a target region comprising a lower bound DVH and an upper bound DVH, a treatment time selector configured to receive user input that specifies a treatment delivery time within a range of treatment times, and a variable dose volume histogram (DVH) for the target region that represents a radiation dose to the target region that corresponds to the specified treatment delivery time. The bDVH may represent a range of radiation dose values to the target region over a range of treatment delivery times. The variable DVH for the target region may be overlaid on the bDVH for the target region (e.g., the variable DVH and bDVH for a target region may be included in the same plot, optionally with shared axes), which may help to highlight the effect of adjusting the treatment delivery time on the dose distribution. The lower bound DVH may correspond to a lower-limit treatment delivery time value and the upper bound DVH may correspond to an upper-limit treatment delivery time value. For example, the lower-limit treatment delivery time value may be a minimum treatment delivery time value, and the upper-limit treatment delivery time value may be a maximum treatment delivery time value. Optionally, the bDVH for the target region may further comprise shading between the upper bound DVH curve and the lower bound DVH curve. The variable DVH curve for the target region may change between the upper bound DVH curve and the lower bound DVH curve according to the user input to the treatment time selector. The treatment time selector may be a graphical slider that is movable between a first limit that corresponds to a low-threshold treatment delivery time value and a second limit that corresponds to a high-threshold treatment delivery time value. Moving the slider to a position between the first and second limits may correspond to selecting the treatment delivery time. Alternatively, the treatment time selector may be a graphical dial that is rotatable between a first limit corresponding to a low-threshold treatment delivery time and a second limit corresponding to a high-threshold treatment delivery time. Setting the dial to a position between the first and second limits may correspond to selecting the treatment delivery time. In some variations, the minimum treatment delivery time value may be determined by generating a fluence map comprising a set of beamlet values by iteratively adjusting the beamlet values based on a cost function comprising a treatment time penalty function such that the fluence map delivers a prescribed dose to the target region and changes of a cost function value between iterations of the beamlet values is less than a selected threshold, and calculating an amount of time to deliver the generated fluence map. The maximum treatment delivery time value may be determined by generating a fluence map comprising a set of beamlet values by iteratively adjusting the beamlet values based on a cost function comprising an organ-at-risk (OAR) dose penalty function such that the fluence map delivers a prescribed dose to the target region and changes of a mean dose to the OAR between iterations of the beamlet values is less than a selected threshold, and calculating an amount of time to deliver the generated fluence map.

In some variations, the GUI may further comprise a second bDVH for a volume of interest (VOI) comprising a second lower bound DVH curve and a second upper bound DVH curve that represent a range of radiation dose values to the VOI over the range of treatment delivery times, and a second variable DVH curve for the VOI that represents a radiation dose to the VOI that corresponds to the specified treatment delivery time. The second variable DVH for the VOI may be overlaid on the second bDVH for the VOI (e.g., the variable DVH and bDVH for a target region may be included in the same plot, optionally with shared axes), which may help the user to directly see how changing the treatment delivery time affects the dose distribution for the VOI. For example, overlaying or superimposing the DVH over the bDVH may help a user to readily identify dose that strays outside the bounds of the bDVH. In some variations, the DVHs of multiple VOIs (e.g., target regions, OARs) may be overlaid with the corresponding bDVHs so that the user can compare the DVHs with the bDVHs for multiple VOIs simultaneously. The second bDVH for the VOI may further comprise shading between the upper bound DVH curve and the lower bound DVH curve. The second variable DVH curve for the VOI may change between the upper bound DVH curve and the lower bound DVH curve of the second bDVH for the VOI according to the user input to the treatment time selector. The VOI may comprise a heart, a spinal cord, and/or an esophagus. Alternatively, or additionally, the VOI may comprise an organ-at-risk (OAR).

In some variations, the GUI may further comprise a third bDVH for a second VOI comprising a third lower bound DVH curve and a third upper bound DVH curve that represent a range of radiation dose values to the second VOI over the range of treatment delivery times, and a third variable DVH curve for the second VOI that represents a radiation dose to the second VOI that corresponds to the specified treatment delivery time. Optionally, the GUI may comprise a DVH-viewer selection menu that may include a graphical selection toggle for each of the first, second and third bDVHs, where a user-selection of a first toggle state displays the corresponding bDVH and a second toggle state hides the corresponding bDVH. The first, second and third bDVHs may each depicted with different colors.

A GUI may further comprise a first text field that indicates a mean dose to the target region and a second text field that indicates a maximum dose to the target region for the specified treatment delivery time. The GUI may also comprise a graphical indicator of the treatment delivery time specified by the treatment time selector. In some variations, the GUI may comprise a command button that is triggers treatment plan optimization with the treatment delivery time specified by the treatment time selector.

Also disclosed herein is a GUI for radiotherapy planning comprising a treatment time axis, a lower limit indicator on the treatment time axis, where the lower-limit indicator is at a minimum treatment time for delivering a prescribed dose to a target region, an upper limit indicator on the treatment time axis, where the upper-limit indicator is at a maximum treatment time for delivering the prescribed dose to the target region, and a treatment time indicator on the treatment time axis between the lower limit indicator and the upper limit indicator. The treatment time indicator may be at an initial treatment time for delivering the prescribed dose to the target region. The initial treatment time may be calculated by generating a fluence map comprising a set of radiation beamlet weights by iteratively adjusting the beamlet weights based on a cost function comprising an OAR penalty function such that the fluence map delivers the prescribed dose to the target region and changes of a cost function value between iterations of the beamlet weights is less than a selected threshold, and calculating an amount of time to deliver the generated fluence map. In some variations, the minimum treatment time may be determined by generating a fluence map comprising a set of beamlet values by iteratively adjusting the beamlet values based on a cost function comprising a treatment time penalty function such that the fluence map delivers the prescribed dose to the target region and changes of a cost function value between iterations of the beamlet values is less than a selected threshold, and calculating an amount of time it takes to deliver the generated fluence map. The maximum treatment time may be determined by generating a fluence map comprising a set of beamlet values by iteratively adjusting the beamlet values based on a cost function comprising an organ-at-risk (OAR) dose penalty function such that the fluence map delivers a prescribed dose to the target region and changes of a mean dose to the OAR between iterations of the beamlet values is less than a selected threshold, and calculating an amount of time to deliver the generated fluence map.

Also disclosed herein are methods for generating and updating a GUI for radiotherapy planning One variation of a method for generating a GUI may comprise generating a first fluence map that delivers a prescribed dose to a target region using a cost function having a plurality of penalty functions including a treatment time penalty function that is more heavily weighted than the other penalty functions, calculating an amount of time $T_{min}$ to deliver the first fluence map, generating a second fluence map that delivers a prescribed dose to a target region and optimizes a dose to a radiation-avoidance region, calculating an amount of time $T_{max}$ to deliver the second fluence map, generating a plurality of fluence maps that have treatment delivery times between $T_{min}$ and $T_{max}$, generating a bounded dose volume histogram (bDVH) for the target region that represents a dose variability across the first fluence map, the second fluence map, and the generated plurality of fluence maps, generating a GUI that comprises the bDVH, a treatment time selector configured to specify a treatment delivery time between $T_{min}$ and $T_{max}$, and a variable DVH curve for the target region that represents a dose to the target region that corresponds to a variable fluence map that has a treatment delivery time that approximates the specified treatment delivery time, and outputting the GUI to a display device. The method may comprise generating a bDVH for the radiation-avoidance region that represents a dose variability between the first fluence map and the second fluence map. Optionally, the method may comprise generating a variable DVH curve for the radiation-avoidance region that represents a dose to the radiation-avoidance region that corresponds to the variable fluence map. The method may further comprise updating the variable DVH for the radiation-avoidance region in response to selections of treatment delivery times as specified by the treatment time selector. In some variations, the method may further comprise updating the variable DVH for the target region in response to selections of treatment delivery times as specified by the treatment time selector. Optionally, methods may further comprise generating a final fluence map based on a final selection of a treatment delivery time by the treatment time selector. In some variations, the first fluence map may comprise a first set of beamlet values, and generating the first fluence map may comprise iteratively adjusting the first set of beamlet values based on the cost function such that the first fluence map delivers a prescribed dose to the target region. The second fluence map may comprise a second set of beamlet values, and generating the second fluence map may comprise defining a second cost function comprising a radiation-avoidance region penalty function and no treatment time penalty function, and optimizing the dose to the radiation-avoidance region comprises iteratively adjusting the second set of beamlet values based on the second cost function such that the second fluence map delivers a prescribed dose to the target region and changes of a mean dose to the radiation-avoidance region between iterations of the beamlet values is less than a selected threshold. Methods may optionally comprise generating additional DVHs corresponding to the additional fluence maps for the target region and/or radiation-avoidance region.

In some variations, generating additional fluence maps may comprise selecting a treatment delivery time $T_{selected}$ that is between $T_{min}$ and $T_{max}$, generating an intermediate fluence map comprising a set of beamlet values by combining the first fluence map and the second fluence map, adjusting the treatment time penalty function of the cost function according to the selected treatment delivery time $T_{selected}$, and generating an additional fluence map for the selected treatment delivery time $T_{selected}$ by iteratively adjusting the beamlet values of the intermediate fluence map based on the adjusted cost function such that the target region receives the prescribed dose and changes of the cost function value between iterations of the beamlet values is less than a selected threshold. In some variations, combining the first fluence map and the second fluence map may comprise generating an approximation of a Pareto optimal fluence map. For example, the approximation of a Pareto optimal fluence map may comprise a convex combination of the first fluence map and the second fluence map. Adjusting the treatment time penalty function may comprise changing the treatment time penalty function from $w \cdot T_{est}$ to $w \cdot |T_{est} - T_{selected}|_1^+$, where w is a weight of the treatment time penalty function, and $T_{est}$ is the treatment time for an iteration of a fluence map. In some variations, the selected treatment delivery time may be halfway between $T_{min}$ and $T_{max}$. In some variations, generating the plurality of fluence maps may comprise calculating a plan quality metric value for each fluence map and defining sub-ranges of treatment delivery times between $T_{min}$ and $T_{max}$ for treatment delivery times that correspond to fluence maps that have plan quality metric values that differ from each other by more than a specified margin. For example, generating the plurality of fluence maps that have treatment delivery times between $T_{min}$ and $T_{max}$ may comprise defining, for each treatment delivery time, a cost function that has a treatment time penalty that includes a treatment time threshold that corresponds with the respective treatment time, and iteratively adjusting fluence map beamlet values based on the defined cost function such that the target region receives the prescribed dose and changes of the cost function value between iterations is less than a selected threshold. In some variations, generating the plurality of fluence maps may further comprise repeatedly defining sub-ranges of treatment delivery times, selecting treatment times within the sub-ranges, generating fluence maps for the selected treatment times, and calculating the plan quality metric value for the generated fluence maps. The plan quality metric value may be calculated from a mean dose to the radiation-avoidance region and/or a cost function value for the fluence map. Some methods may further comprise updating the variable DVH curve for the target region in response to an updated treatment delivery time specified by the treatment time selector. Updating the variable DVH may comprise interpolating between DVHs that correspond to fluence maps that have treatment delivery times that bound the updated treatment delivery time. Alternatively, or additionally, updating the variable DVH may comprise interpolating between fluence maps that have treatment delivery times that bound the updated treatment delivery time to generate an interpolated fluence map, and generating the updated variable DVH from the interpolated fluence map. Some variations may further comprise calculating mean doses to the target region and the radiation-avoidance region and calculating maximum doses to the target region and the radiation-avoidance region, and the GUI may comprise a text field that displays the mean and maximum doses for the target region and the radiation-avoidance region, and updating the variable DVH curve may further comprise updating the mean and maximum doses for the target region and the radiation-avoidance region.

BRIEF DESCRIPTION OF THE DRAWINGS

FIG. 1H depicts a flowchart representation of one variation of a method of using a GUI to facilitate fluence map optimization based on a selected treatment time.

FIG. 2 depicts one variation of a GUI that plots an initial treatment time relative to minimum and maximum treatment times.

FIG. 3 depicts a flowchart representation of one variation of a method for generating a radiotherapy planning GUI that depicts radiation dose information in relation to various treatment delivery times.

FIG. 4A depicts a flowchart representation of one variation of a method for generating a fluence map that has a treatment delivery time that may be a lower limit of a range of treatment times.

FIG. 4B depicts a flowchart representation of one variation of a method for generating a fluence map that has a treatment delivery time that is may be an upper limit of a range of treatment times.

FIG. 5 depicts a flowchart representation of one variation of a method for selecting treatment times within a range of treatment times and generating fluence maps that have treatment delivery times that correspond to the selected treatment times.

FIG. 7 depicts a flowchart representation of one variation of a method for generating a GUI that comprises a plot of the initial treatment time (e.g., a fluence map with a particular cost function) relative to minimum and maximum treatment times.

DETAILED DESCRIPTION

Figure 1A:
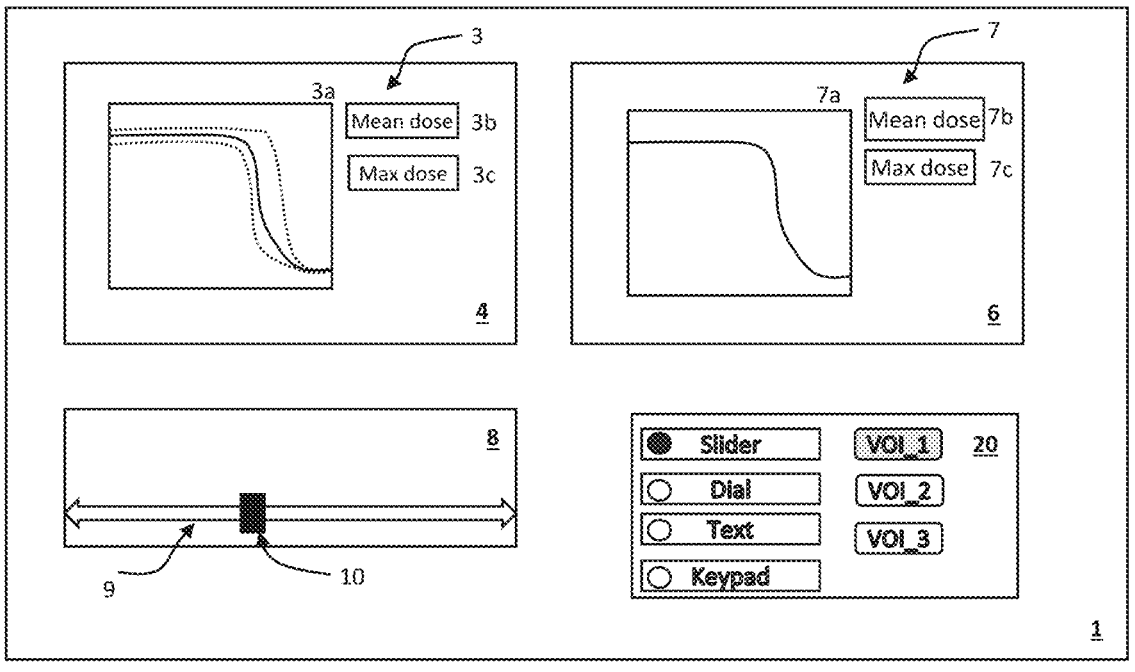
FIG. 1A depicts a block diagram representation of one variation of a graphical user interface (GUI).

During treatment planning, a clinician reviews planning images (e.g., CT images, PET images, MR images, etc.) and contours the target regions and radiation-avoidance regions, which are collectively referred to herein as volumes of interest (VOIs). Examples of VOIs may include tumors, a volumetric shell around the tumor that accounts for positional changes and/or uncertainties and/or microscopic disease at the edges of a tumor (e.g., gross tumor volume (GTV), clinical target volume (CTV), planning target volume (PTV), internal target volume (ITV)), organs-at-risk (OARs), and/or any contoured volume defined by a clinician. They may also define the dose objectives for each of the contoured regions. For example, the clinician may set the radiation dose to each target region (i.e., a prescribed dose and/or a range of acceptable dose values), and may also set limits on the radiation dose to each radiation-avoidance region (e.g., a maximum dose that is considered "safe"). The goal of treatment planning is to generate a fluence map that delivers the prescribed dose to the one or more target regions, while minimizing undesirable irradiation characteristics. Examples of undesirable irradiation characteristics may include, for example, excessive dose to OARs, a non-smooth fluence map (e.g., high gradient of change between beamlet values of a fluence map), prolonged treatment time, etc. Treatment planning may comprise defining a cost function, which comprises a plurality of penalty functions that may discourage these (and other) undesirable treatment characteristics. In some variations, the penalty functions may be weighted relative to each other, reflecting the priority or importance of the penalty functions. The value of a cost function may be calculated for a fluence map, and may be a score that indicates how well the fluence map "avoids" the undesirable characteristics. For example, a fluence map that has a high cost function value indicates that fluence map has a greater prevalence of the undesirable characteristics as compared to a fluence map that has a low cost function value. Ideally, the radiotherapy planning system generates a fluence map that meets the dose objectives while minimizing the value of the cost function. Fluence map optimization is an iterative process by which beamlet values of the fluence map are adjusted to find the beamlet values that meet dose objectives while minimizing the cost function.

Since the generation of a fluence map is guided by a cost function, changing the definition of any one penalty function of the cost function and/or its weight relative to the other penalty functions may affect the beamlet values of the resultant fluence map, and therefore, affect the radiation dose to the VOIs. However, due to the complexity of the cost function, dose objectives, number of VOIs, and other treatment parameters, it may be difficult for a clinician to evaluate how changing one optimization parameter, such as one particular penalty function, may affect the radiation dose to the VOIs, and whether that dose effect is acceptable. For example, a clinician may wish to vary the treatment time (e.g., constrain it so that it does not exceed an upper limit) of a fluence map, and evaluate whether increasing or decreasing the treatment time affects the dose certain OARs more than others, and whether that dose effect is acceptable. Furthermore, optimizing the fluence map for every adjustment to a penalty function can be computationally intensive and time consuming.

Described herein are various radiotherapy planning system graphical user interfaces (GUI) and methods for calculating and displaying radiation dose information. One variation of a GUI may provide a user with the option of selecting a treatment time and to display the radiation dose information of one or more VOIs that corresponds to the selected treatment time. The "treatment time" or "treatment delivery time" for a given radiation fluence map is the amount of time it would take for a radiotherapy system to emit the radiation beamlets specified by the fluence map during a treatment session (i.e., a single fraction). That is, treatment time may refer to the duration of time that the radiotherapy system would need to be emitting radiation in order to deliver the fluence map. In some cases, a fluence map that has a longer treatment time may provide better dose characteristics (e.g., more conformal dose, providing the prescribed dose to tumors while reducing the irradiation of surrounding tissue) than a fluence map that has a shorter treatment time. The GUI may dynamically update (e.g., in real-time) the radiation dose information for one or more VOIs as the user selects different treatment time values. In some variations, the GUI may comprise a first graphic that represents a range of treatment times and a second graphic that represents the range of radiation dose values to the one or more VOIs that corresponds with that range of treatment of times. This may help the user to understand the tradeoff between the treatment time and the dose delivered by the treatment plan. In some variations, the "quality" of the dose delivered by the fluence map of a treatment plan may be evaluated based on the amount of radiation received by one or more OARs during the delivery of prescribed radiation to the one or more tumors.

The treatment time and dose information displayed on the GUI may help the user to control or determine the treatment time that provides the appropriate radiation dose to the VOIs. Once the user finalizes the treatment time selection, the radiotherapy planning system may then incorporate the final, selected treatment time into a treatment time penalty function of an optimization cost function, and generate a fluence map by iteratively adjusting the beamlet weights of the fluence map based on the cost function until the resultant fluence map is one that delivers a prescribed dose to a target region within the treatment time selected by the user. The GUI and methods described herein may be used before fluence map optimization to help define the cost function (e.g., by specifying a value or range of values of penalty function weights) and/or may be used as part of fluence map optimization (e.g., between iterations of the optimization, as a final step in the last iteration prior to generating the final fluence map). In some variations, the method may comprise calculating dose information (e.g., mean dose, max dose, DVHs) from the final fluence map for each of the VOIs, and updating the GUI to display the dose information and the corresponding treatment time.

Also described herein are methods for generating a GUI of treatment time and dose information such that updating the dose information based on user-specified treatment time(s) does not require multiple manual optimization iterations. One variation of a method for generating the GUI comprises defining a range of treatment times (e.g., selecting a minimum treatment time $T_{min}$ and a maximum treatment time $T_{max}$), calculating fluence maps and corresponding dose information for a selection of treatment times within the range of treatment times (including for the minimum treatment time $T_{min}$ and the maximum treatment time $T_{max}$), and generating a dose graphic that represents the dose variability across the range of treatment times. In some variations, the generation of a fluence map for a particular treatment time may comprise using a weighted combination of fluence maps that were previously generated for other treatment times. The dose graphic may be generated using the fluence maps generated for the selection of treatment times. The GUI may comprise the dose graphic, a treatment time selector that is configured to receive user input that specifies a treatment time, and a variable dose graphic that reflects the dose information that corresponds to the specified treatment time. Examples of dose graphics may comprise a DVH, a bounded DVH (bDVH), mean dose, minimum dose, and/or maximum dose to one or more VOIs.

The user may change the treatment time using the treatment time selector and the GUI may be dynamically updated so that the variable dose graphic reflects the dose delivered to one or more VOIs for the updated treatment time. For example, the dose graphic may comprise a bDVH that represents the dose variability across the range of treatment times and the variable dose graphic may comprise a DVH that represents the dose that corresponds to the specified treatment time. The variable dose graphic may be generated using the fluence maps and/or dose information that were calculated during the generation of the GUI. In some variations, dynamically updating the dose graphics for a user-selected treatment time within the range of treatment times may comprise interpolating between the previously generated fluence maps and/or dose information, and/or may comprise generating a convex combination of the previously generated fluence maps and/or dose information. Updating the dose information for a selected treatment time using previously generated fluence maps and/or dose information may facilitate rapid updates to the dose graphic(s) without requiring computationally intensive calculations (such as fluence map optimization).

Graphical User Interface Depicting Dose and Treatment Time

FIG. 1A is a block diagram representation of one variation of a GUI. In this variation, a GUI (2) may comprise a dose graphic (4), a variable dose graphic (6), and a treatment time selector (8). The treatment time selector may be a graphical input that allows a user to select a desired treatment time. In some variations, the treatment time selector (8) may indicate a range (9) of treatment times so that the user is limited to selecting a treatment time within that range. The dose graphic (4) may comprise one or more dose metrics (3) for the one or more VOIs that may represent the range of radiation dose values to the VOI(s) over the range of treatment times. For example, a dose graphic (4) for a VOI may comprise one or more of a bDVH, a DVH, a mean dose value, a minimum dose value, a maximum dose value, etc. The GUI (2) may comprise a dose graphic (4) that includes a bDVH (3a) and text fields that display the mean dose (3b) and maximum dose (3c) for a VOI at a selected treatment time. The variable dose graphic (6) may comprise a dose metric (7) for the one or more VOIs that represents the radiation dose value to the VOI(s) for the treatment time that has been selected by the user via the treatment time selector. The dose metric value(s) of the variable dose graphic may be updated whenever the user inputs a different treatment time via the treatment time selector. In some variations, at least a portion of the variable dose graphic may be superimposed or overlaid with at least a portion of the dose graphic. For example, the variable dose graphic comprising a DVH may be superimposed over the dose graphic comprising a bDVH, which may allow a user to compare the dose distribution of a fluence map having the selected treatment time with the dose distribution of fluence maps that have a range of treatment delivery times. This may help the user to directly see how changing the treatment delivery time affects the dose distribution. For example, overlaying or superimposing the DVH over the bDVH may help a user to readily identify dose that strays outside the bounds of the bDVH. In some variations, the DVHs of multiple VOIs (e.g., target regions, OARs) may be overlaid with the corresponding bDVHs so that the user can compare the DVHs with the bDVHs for multiple VOIs simultaneously.

Figures 1B, 1C, 1D:
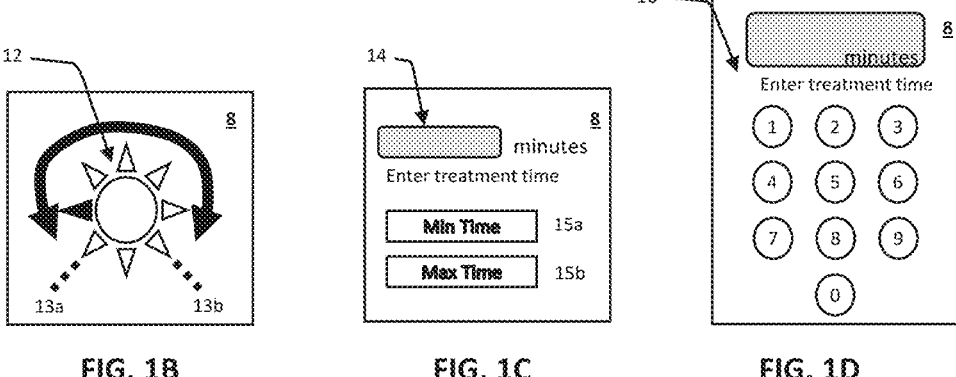
FIGS. 1B-1D depict variations of a graphical treatment time selector.

In one variation of a GUI, the treatment time selector (8) may comprise a graphical slider (10) that is movable between a lower limit and an upper limit (i.e., range of treatment times), where the position of the slider represents a selection of a treatment time. Alternatively, as shown in FIG. 1B, the treatment time selector may comprise a graphical dial (12) that is rotatable between a lower limit (13a) and an upper limit (13b), where the radial position of the dial (e.g., angular location between 0° and 360° or a subset of an angular range between 0° and) 360° represents a selection of a treatment time. In some variations, the treatment time selector (8) may comprise an input text field (14) that is configured to receive numerical text entered by the user that indicates the desired treatment time, as shown in FIG. 1C. FIG. 1D depicts a treatment time selector (8) that comprises a numerical keypad (16) that where the user can enter the numbers that specify the desired treatment time. A treatment time selector comprising an input text field or a keypad may optionally comprise one or more text fields that display a range of selectable treatment times and if the user enters a treatment time that is outside of the range of treatment times, the radiotherapy planning system may then generate a notification that the treatment time is out-of-range. For example, the lower limit of the range of selectable treatment times may be displayed in a first text field that is labeled as "minimum treatment time" and the upper limit of the range may be displayed in a second text field that is labeled as "maximum treatment time". FIG. 1B depicts an example of a treatment time selector that optionally comprises text fields that indicate the minimum selectable treatment time ($15a$) and the maximum selectable treatment time ($15b$). In some variations, there may be display setting (20) that allows a user to select their preferred treatment time selector graphic (e.g., to select between a slider, dial, or text box), and/or select one or more VOIs for which dose graphics and variable dose graphics are to be included in the GUI. The lower limit may correspond to a lower bound on treatment time ($T_{min}$) while the upper limit may correspond to an upper bound on treatment time ($T_{max}$). In some variations, the lower bound on treatment time may be a treatment time below which a fluence map would fail to meet dose objectives, for example, failing to deliver the prescribed dose(s) to the target region(s) and/or exposing OARs to radiation levels that are higher than a predetermined threshold. The upper bound on treatment time may be a treatment time that exceeds what is clinically acceptable (e.g., longer than a patient is able to tolerate treatment immobilization, longer than allocated treatment session time slots, etc.) and/or may be the threshold beyond which further increases in treatment time result in little, if any, improvements in treatment plan quality.

Figure 1E:
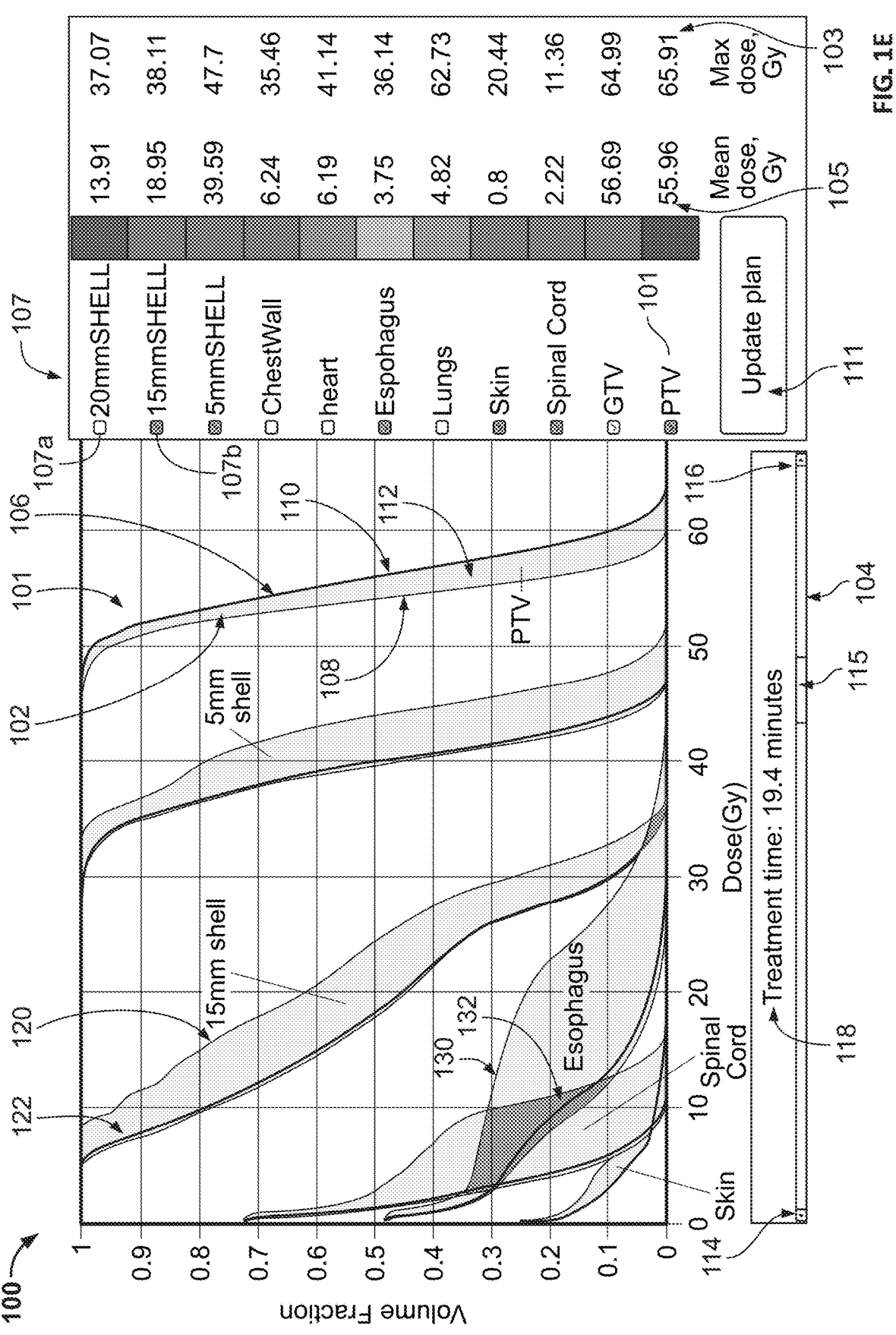
FIG. 1E depicts one variation of a GUI.

FIG. 1E depicts one variation of a radiotherapy planning system graphical user interface (GUI). The GUI (100) may comprise a dose graphic (102) for a target region (101), a treatment time selector (104), and a variable dose graphic (106) for the target region that is overlaid on the dose graphic (e.g., the variable DVH and bDVH for a target region may be included in the same plot, optionally with shared axes). In this variation, the dose graphic (102) for the target region is a bounded DVH (bDVH) and the variable dose graphic (106) is a DVH curve that is within the bounds of the bDVH. The treatment time selector (104) may comprise a slider that is movable between a lower limit (114) and an upper limit (116) of a range of treatment times. The position of the slider relative to the lower and upper limits specifies the treatment time (which is, in this example, 19.4 minutes). The bounded DVH (102) may comprise a lower bound DVH (108) and an upper bound DVH (110). The bDVH (102) may comprise a shaded region (112) between the lower bound DVH (108) and the upper bound DVH (110), which may help visually highlight the range of dose distribution variability for the target region (101) across a range of treatment times. Optionally, the variable dose graphic may comprise text fields that indicate a maximum dose (Gy) value (103), mean dose (Gy) value (105), and/or a minimum dose (Gy) value to the target region (101) for the selected treatment time. The DVH (106) and/or dose text fields (103, 105) may change when the user selects different treatment times using the selector (104). In some variations, the DVH (106) and/or dose text fields (103, 105) for the target region may update dynamically as the user moves the slider between the upper and lower limits. Overlaying the variable dose graphic with the dose graphic may help the user to directly see how changing the treatment delivery time affects the dose distribution. For example, overlaying or superimposing the DVH over the bDVH may help a user to readily identify dose that strays outside the bounds of the bDVH.

A GUI may comprise dose graphics and variable dose graphics for other VOIs so that a user can see how adjusting the treatment time affects the dose to those VOIs. For example, a GUI may comprise a dose graphic for a 5 mm shell, 15 mm, and/or 20 mm shell around the target region (denoted here as the PTV volume), and/or a dose graphic for one or more OARs, such as the heart, esophagus, lungs, skin, and spinal cord. Graphical user interface (100) may comprise a bDVH (120) and DVH (122) for a 15 mm shell around the target region and a bDVH (130) and a DVH (132) for the esophagus. The bDVHs (120, 130) may each comprise a shaded region (124, 134) that extends between the lower bound and upper bound DVHs that represents the dose distribution variability for the 15 mm shell and the esophagus as a function of treatment time. The DVH (122, 132) for the 15 mm shell and the esophagus may change when the user selects a different treatment time using the treatment time selector. In some variations, the DVHs (122, 132) for the 15 mm shell and the esophagus may update dynamically as the user moves the slider between the upper and lower limits. The dose text fields (mean dose, maximum dose) to the 15 mm shell and the esophagus may also be updated when the user specifies a different treatment time. Overlaying the DVHs of multiple VOIs (e.g., target regions, OARs) with the corresponding bDVHs may help the user to compare the DVHs with the bDVHs for multiple VOIs simultaneously, which may help generate a qualitative sense of how the treatment time affects multiple VOIs overall.

Figure 1F:
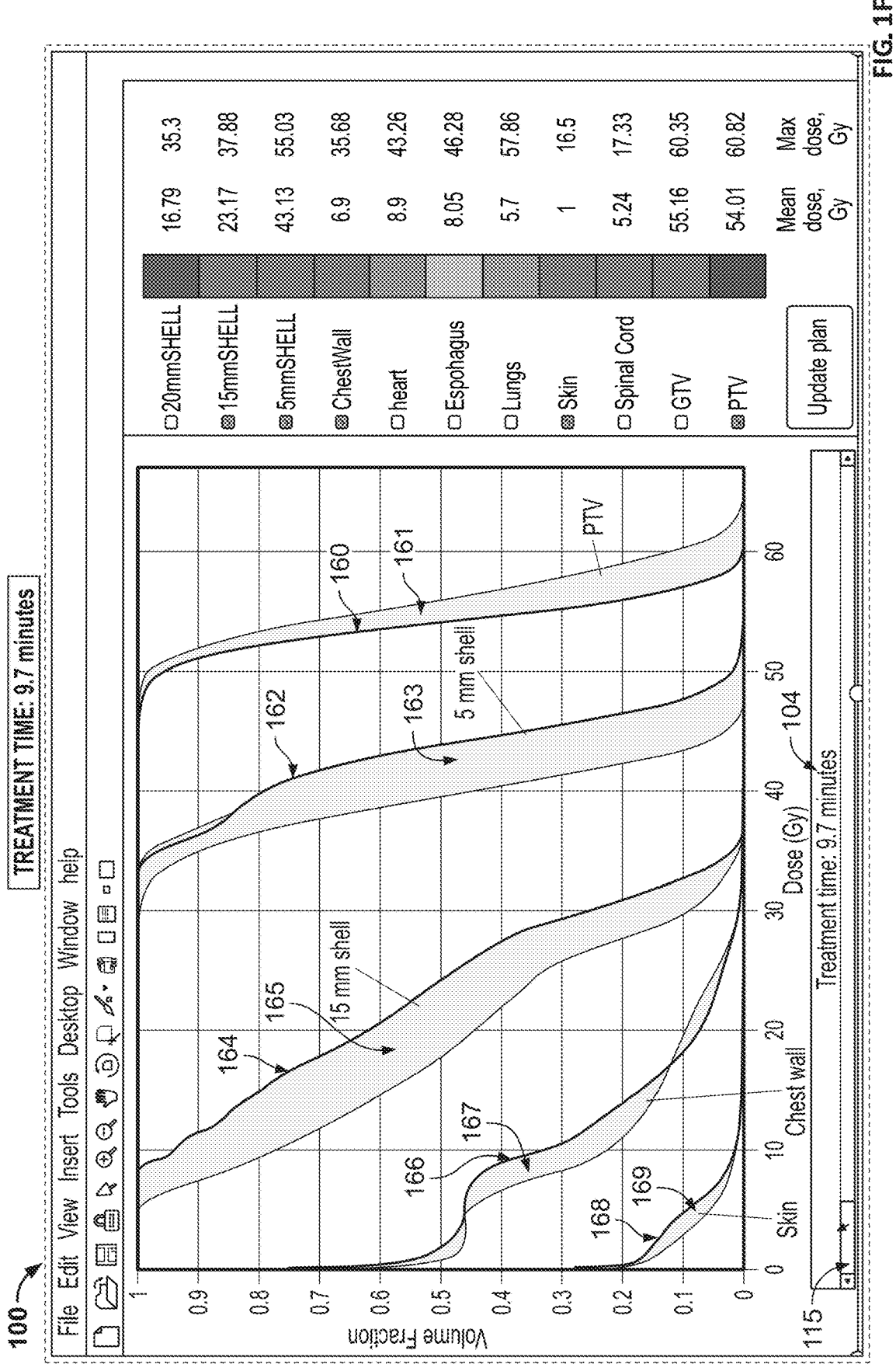
FIG. 1F depicts a GUI where the selected treatment time is 9.7 minutes and the GUI displays dose metrics and variable dose graphics for a fluence map that has a treatment time of 9.7 minutes.
Figure 1G:
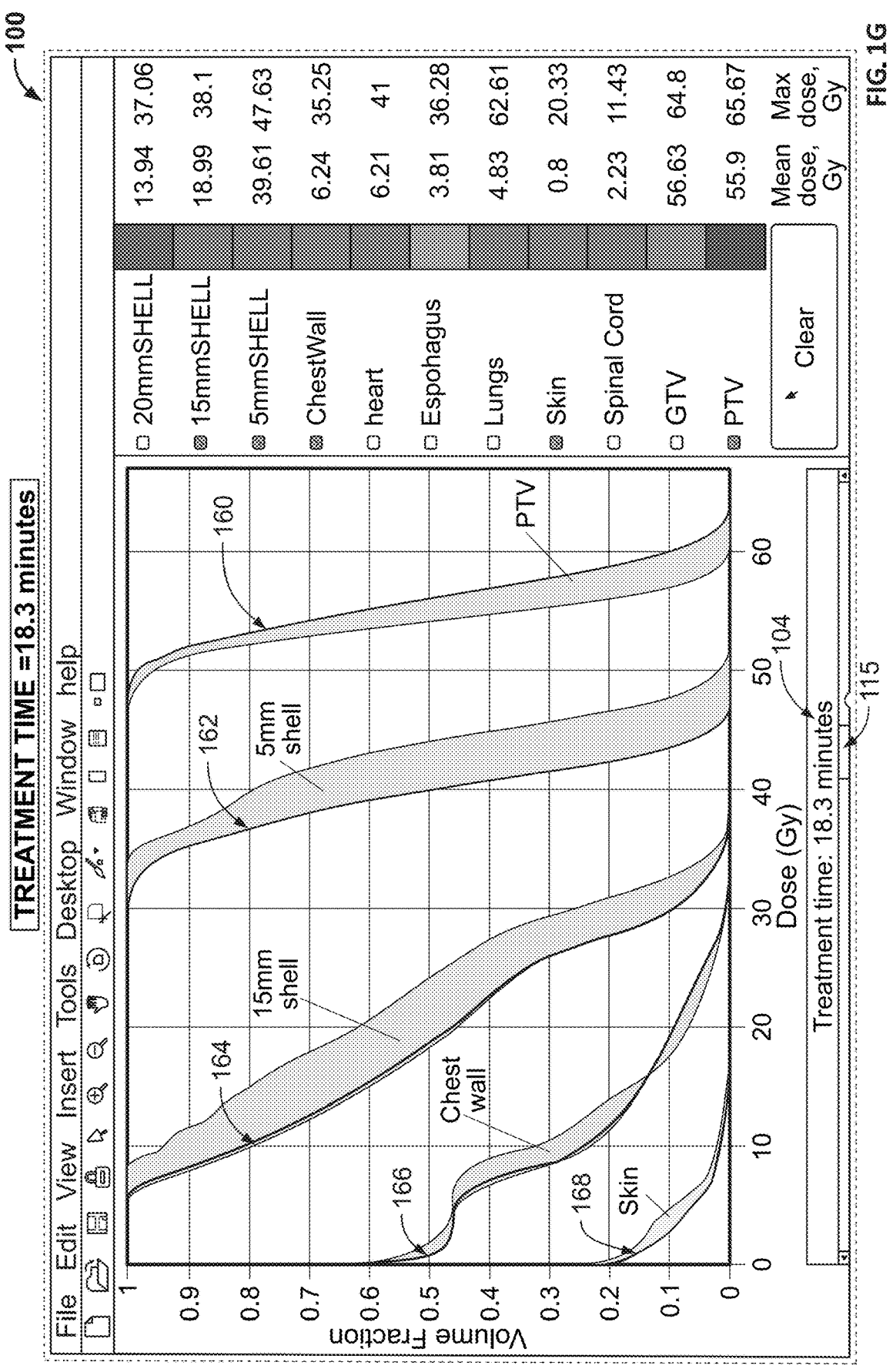
FIG. 1G depicts a GUI where the selected treatment time is 18.3 minutes and the GUI displays dose metrics and variable dose graphics for a fluence map that has a treatment time of 18.3 minutes.

FIGS. 1F and 1G depict the GUI (100) as it changes for different treatment times selected by the user. GUI (100) comprises a treatment time selector (104) with a slider (115) that may be moved by the user to select a treatment time, dose graphics that comprise bDVH curves and variable dose graphics comprising DVH curves. The GUI in both FIGS. 1F and 1G have the same bDVHs with the shaded regions representing the dose variability across the range of treatment times. For example, GUI (100) depicts a bDVH for the PTV (161), a bDVH for the 5 mm shell (163), bDVH for the 15 mm shell (165), bDVH for the chest wall (167), and a bDVH for the skin (169). As the user selects different treatment times using the slider (115), the variable dose graphic changes. In FIG. 1F, the selected treatment time is 9.7 minutes while in FIG. 1G, the selected treatment time is 18.3 minutes. The methods described herein may be used to calculate the variable dose graphic (which includes a DVH curve, mean dose and max dose, in this example) for a fluence map with a treatment delivery time of 9.7 minutes and a fluence map with a treatment delivery time of 18.3 minutes. As shown in FIG. 1F (treatment time=9.7 minutes), the DVH curve for the 5 mm shell (162), and the DVH curve for the 15 mm shell (162), along with the DVH curve for the chest wall (166) and the DVH curve for the skin (168), are all at or close to the upper bound of their respective bDVHs, while the DVH curve for the PTV (160) is at or near the lower bound of its bDVH (161). In FIG. 1G (treatment time=18.3 minutes), the DVH curve for the 5 mm shell (162), and the DVH curve for the 15 mm shell (162), along with the DVH curve for the chest wall (166) and the DVH curve for the skin (168), are all at or close to the lower bound of their respective bDVHs, while the DVH curve for the PTV (160) is at or near the upper bound of its bDVH (161). By nearly doubling the treatment time, the dose to the PTV is increased while the dose to the surrounding tissue (e.g., shells, chest, skin, etc.) are decreased. The user may move the slider (115) to select other treatment times and the GUI (100), using the methods described herein, may dynamically (e.g., in real-time) update the variable dose graphic to reflect the impact of treatment time on the dose distribution.

The treatment time selector (104) of the GUI (100) may comprise a slider (115) that the user may move between the lower limit (114) and the upper limit (116). A text field (118) may be updated with the value of the treatment time as the slider (115) is being moved and/or when the slider (115) is stopped at a location between the lower and upper limits. Optionally, the treatment time selector may include additional text boxes in the vicinity of the upper and lower limits (114, 116) that indicate the treatment time value at each of the limits. Alternatively, the treatment time selector may be a dial, where the rotation of the dial is bounded by upper and lower limits so that the user may specify a treatment time within the range of treatment times. In other variations, the treatment time selector may comprise an input text field or a numerical keypad.

A GUI may also comprise a dose graphic viewer selection menu that comprises a selection toggle for each of the dose graphics. A user may use the selection toggles to indicate the VOIs for which they wish to view dose information. For example, the GUI may display the dose graphics and variable dose graphics only for the VOIs that have been selected by the user. For example, GUI (100) may comprise a DVH-viewer selection menu (107) that comprises a toggle or check box for each VOI. The VOI "20 mm shell" may have its own toggle (107a) and the "15 mm shell" may have its own toggle (107b). As exemplified in FIG. 1A, the "20 mm shell" toggle (107a) is not selected and the "15 mm shell" toggle (107b) is selected, resulting in the display of the dose graphic and variable dose graphic for the "15 mm shell" but hiding the dose graphic and variable dose graphic for the "20 mm shell". In some variations, the mean dose and maximum dose graphics are always displayed, regardless of the toggle state for its respective VOI, while in other variations, the mean dose and maximum dose graphics may be displayed or hidden as indicated by the viewer selection menu. The dose graphics and variable dose graphics for various VOIs may have different colors or line weights and patterns, as may be desirable.

The GUI may comprise a command button that triggers the radiotherapy planning system to optimize the treatment plan with the treatment time specified by the treatment time selector. As an example, the GUI (100) may comprise an "Update plan" button (111) that initiates a fluence map optimization algorithm using a cost function that includes a treatment time penalty function that incorporates the user-specified treatment time. After the radiotherapy planning system generates a fluence map that has been optimized using the user-specified treatment time, the dose graphics and variable dose graphics of the GUI may be updated according to the newly generated fluence map. The clinician may review the dose information for one or more of the VOIs and provide their approval of the fluence map. Alternatively, or additionally, the GUI may be used to help define the cost function at the start of fluence map optimization (e.g., before any fluence map iterations, or as part of the first few fluence map iterations) or may be used toward the end of fluence map optimization (e.g., during the last few fluence map iterations, or as the last fluence map iteration) to generate the final fluence map.

Method of Using a Graphical User Interface Depicting Dose and Treatment Time

The GUIs described herein may be used to help facilitate the fluence map optimization phase of radiotherapy treatment planning, and may be used, for example, to guide the selection of a treatment time that is clinically acceptable and generate a fluence map that meets dose objectives for the VOIs. FIG. 1H depicts one variation of a method of using a GUI to facilitate fluence map optimization based on a selected treatment time. Method (140) may comprise receiving (142) a selection of a treatment time within a range of treatment times (e.g., between $T_{min}$ and $T_{max}$), updating (144) the dose graphic(s) to one or more target regions and/or one or more OARs according to the selected treatment time, and outputting (146) the updated dose graphic(s) to one or more target regions and/or one or more OARs to a display device. The user may view the dose graphic(s) in conjunction with the corresponding treatment time and may decide to select a different treatment time, i.e., repeating steps (142-146) as many times as desired. Method (140) may then comprise receiving (148) a command input to initiate fluence map optimization using a cost function comprising a treatment time penalty function that incorporates the selected treatment time value, updating (150) the dose graphic(s) to one or more target regions and/or one or more OARs according to the generated fluence map, and outputting (152) the updated dose graphic(s) to one or more target regions and/or one or more OARs and the corresponding treatment time to the display device. In some variations, the dose graphic(s) may comprise a dose distribution plot such as a DVH, bDVH, and/or text fields that display dose metrics such as minimum dose, maximum dose, and/or mean dose. Method (140) may be used with any of the GUIs described herein, including, for example, the GUI depicted in FIGS. 1A-1G. While method (140) may be used toward the end of fluence map optimization (e.g., during the last few fluence map iterations, or as the last fluence map iteration) to generate the final fluence map, it should be understood that method (140) may be used at the start of fluence map optimization (e.g., before any fluence map iterations, or as part of the first few fluence map iterations).

In some variations, a radiotherapy treatment planning may comprise generating a fluence map by iteratively adjusting the beamlet values of the fluence map based on a cost function that includes various penalty functions, one of which may be a treatment time penalty function that incurs a penalty only if the estimated treatment time exceeds a treatment time threshold. The resulting fluence map may have a treatment time (i.e., duration) that falls within a range of treatment planning times, where the lower limit of that range may be a minimum treatment time associated with a fluence map that delivers a prescribed dose to the target region(s) and the upper limit of that range may be a maximum treatment time associated with a fluence map that delivers the prescribed dose to the target region(s) and where the mean dose to OAR(s) stabilizes at an acceptable clinical level. The treatment time of the resulting fluence map (which may be referred to as an initial treatment time) may be plotted relative to the minimum and maximum treatment times. Its position relative to the minimum and maximum treatment times may indicate whether increasing the threshold for the treatment time penalty function would be likely to substantially improve the characteristics of the dose delivered to one or more of the VOIs. Radiotherapy treatment planning may comprise determining whether the dose delivered by a fluence map having a particular treatment time is clinically acceptable, and if not, adjusting the parameters of the optimization to generate an alternate fluence map. In some variations, adjusting the parameters of the optimization may comprise adjusting one or more of the penalty functions of the cost function. For example, after viewing the GUI plotting the initial treatment time relative to minimum and maximum treatment times, and the resultant VOI dose(s), a clinician may decide to adjust the treatment time penalty function. In a situation where the initial treatment time is closer to the minimum treatment time than it is to the maximum treatment time, it may be that increasing the threshold of the treatment time penalty function may result in a fluence map with better dose characteristics (e.g., meeting dose objectives, delivering prescribed dose to targets and minimizing irradiation of non-targets). Alternatively, if the initial treatment time is closer to the maximum treatment time than it is to the minimum treatment time, it may indicate that further increases in the threshold of the treatment time penalty function will result in a fluence map that has little, if any, improvement to its dose characteristics. This may encourage the clinician to adjust other penalty functions to obtain a desired dose for the VOI(s).

An example of a GUI that comprises a plot of the initial treatment time relative to minimum and maximum treatment times is depicted in FIG. 2. The GUI (200) may comprise a treatment time axis (202), a lower limit indicator (204), an upper limit indicator (206), and a treatment time indicator (208). The treatment time indicator (208) may comprise a graphic element that is located along the treatment time axis (202), and may represent the treatment time of a fluence map generated during treatment planning using an initial cost function. In some variations, radiotherapy treatment planning may comprise generating different fluence maps by adjusting the cost function to reflect different treatment parameters. For example, adjusting the cost function may comprise changing the weights and/or the definition of one or more penalty functions of the cost function. In the variations described herein, different fluence maps may be generated by adjusting the treatment time penalty function(s) of the cost function. A radiotherapy treatment planning system may calculate a lower limit on treatment time (e.g., the treatment time for delivering a fluence map that delivers the prescribed dose to a target region may be a "minimum" treatment time) and represent the calculated lower limit as an indicator (204). A radiotherapy treatment planning system may calculate an upper limit on treatment time (e.g., the treatment time for delivering a fluence map that delivers the prescribed dose to a target region while delivering a reduced quantity to an OAR may be a "maximum" treatment time) and represent the calculated upper limit as an indicator (206). The treatment time indicator (208) may represent the delivery time of a fluence map that is being considered, and may be represented by a graphic element that is different from the graphic element(s) of the lower limit indicator (204) and the upper limit indicator (206). In some variations, there may be a plurality of treatment time indicators (208) that represent the treatment times/durations of a plurality of fluence maps. This may facilitate the comparison of the fluence maps and help a clinician select a fluence map for further consideration. Methods for generating the GUI of FIG. 2 are described further below.

Methods of Generating a Graphical User Interface for Optimizing Dose and Treatment Time One variation of a method for generating a radiotherapy planning GUI that depicts radiation dose information in relation to various treatment delivery times may comprise generating a set of fluence maps that have treatment delivery times between a lower treatment time limit and an upper treatment time limit, generating bDVHs for each of the VOIs that represents the dose variability across the range of treatment times, and outputting a GUI that comprises the generated bDVHs and a treatment time selector to a display device. Optionally, DVHs for each of the VOIs may be calculated for each fluence map in the set of fluence maps. The method may also comprise calculating a variable DVH for each of one or more VOIs based on the fluence map that has a treatment time that approximates a treatment time selected by the treatment time selector and overlaying the variable DVH onto the generated bDVHs of the corresponding VOIs. One variation of dynamically updating the radiation dose information of the GUI in response to the selection of various treatment delivery times may comprise generating a fluence map that has a treatment delivery time that approximates the selected treatment time, calculating updated variable DVHs for the one or more VOIs, updating the GUI with the updated variable DVHs, and outputting the updated GUI to a display device. In some variations, generating a fluence map that has a treatment delivery time that approximates the selected treatment time may comprise determining whether the fluence map that has a treatment delivery time that approximates the selected treatment time has already been calculated and if the fluence map has already been generated (i.e., is within the set of generated fluence maps), updating the variable DVHs of the GUI with the DVHs calculated from the fluence map, and outputting the updated GUI to the display device. However, if a fluence map having a treatment delivery time that approximates the selected treatment time has not already been generated (i.e., is not within the set of generated fluence maps), the method may comprise generating an intermediate fluence map that is an interpolation (e.g., a linear interpolation, convex interpolation) of two or more fluence maps in the set of fluence maps that have treatment delivery times that bound the selected treatment time, updating the variable DVHs of the GUI with the DVHs calculated from the intermediate fluence map, and outputting the updated GUI to the display device. In variations where DVHs for the VOIs were calculated for the fluence maps in the set of fluence maps, updating the radiation dose information of the GUI in response to the selection of various treatment delivery times may comprise generating intermediate DVHs for the VOIs that are calculated by interpolating (e.g., a linear interpolation, convex interpolation) two or more DVHs that have treatment delivery times that bound the selected treatment time, updating the variable DVHs of the GUI with the intermediate DVHs, and outputting the updated GUI to the display device.

FIG. 3 depicts a flowchart representation of one variation of a method for generating a radiotherapy planning GUI that depicts radiation dose information in relation to various treatment delivery times. Method (300) may comprise generating (302) a first fluence map that delivers a prescribed dose to a target region using a cost function having a plurality of penalty functions including a treatment time penalty function that is more heavily weighted than the other penalty functions, calculating (304) an amount of time $T_{min}$ for delivering the first fluence map, generating (306) a second fluence map that delivers a prescribed dose to a target region and optimizes an OAR dose metric, calculating (308) an amount of time $T_{max}$ for delivering the second fluence map, generating (310) additional fluence maps that have treatment delivery times between $T_{min}$ and $T_{max}$, generating (312) bDVH(s) for the target region and/or the OAR that represents a dose variability across the generated fluence maps, generating (314) a graphical user interface that comprises the bDVH(s) for the target region and/or OAR, a treatment time selector that specifies a treatment delivery time, and a variable DVH curve for the target region and/or OAR that represents the dose(s) to the target region and/or OAR that corresponds to a variable fluence map that has a treatment delivery time that approximates the specified treatment delivery time, and outputting (316) the generated graphical user interface to a display device.

The treatment delivery time for a particular fluence map may be specific for the radiotherapy system that will be used to deliver the therapeutic radiation to the patient, and thus, the treatment delivery time may vary for different radiotherapy systems. In some variations, calculating the treatment delivery time (304, 308) may comprise the radiotherapy treatment planning system being provided with certain parameters of the beam generation, beam delivery, and/or patient couch parameters of a radiotherapy system to calculate the amount of time it would take to deliver the fluence map. For example, the radiotherapy treatment planning system may be provided with data such as the amount of dose delivered per therapeutic radiation pulse (e.g., per linear accelerator pulse, electron gun pulse, etc.), the number of pulses the system is able to deliver for each position of the therapeutic radiation source, the speed with which the radiation source may be moved from one position to another, the number of patient couch positions, the dwell time at each couch position (also referred to as a "beam station"), the distance between couch positions, and/or the speed with which the couch may be moved to each of the couch positions. For a radiotherapy system comprising a therapeutic radiation source that is mounted on a circular rotatable gantry (e.g., that may be able to rotate continuously around the couch), the amount of time for the therapeutic radiation source to complete a single revolution may also be provided to the planning system. These parameters may be derived from simulation data and/or experimental data (e.g., actual measurements taken from the radiotherapy system). In one variation, the treatment delivery time for a fluence map may be calculated by determining the dwell time for each couch beam station based on the number and duration of linac pulses, and the number of linac positions and/or rotations about the couch, adding any linac travel time, and adding the couch travel time between each couch beam station. The fluence map may be divided on a per-beam station basis, and for each beam station, the planning system may extract the largest amount of fluence to be emitted at that beam stations, calculate the number of linac pulses and the number of gantry rotations to deliver that fluence, and multiply the number of gantry rotations with the rotation period (i.e., amount of time to complete on gantry revolution) to calculate the dwell time at a beam station. The treatment delivery time may be calculated by summing all of the beam station dwell times and the couch travel time between each beam station.

Calculating a DVH from a fluence map may comprise converting the fluence map into a dose distribution for a VOI using a dose calculation matrix (which maps the dose delivered to each voxel in a VOI by each beamlet in the fluence map), and generating a histogram for each dose level that indicates the number of voxels in the VOI that meets or exceeds that dose level. In some variations, generating (312) a bDVH for a VOI may comprise calculating a lower bound DVH that corresponds with the first fluence map (which is deliverable in treatment time $T_{min}$) and calculating an upper bound DVH that corresponds with the second fluence map (which is deliverable in treatment time $T_{max}$). Alternatively, the lower bound DVH may correspond with the right-most DVH of the generated fluence maps and the upper bound DVH may correspond with the left-most DVH of the generated fluence maps. For example, generating the lower bound DVH for a bDVH may comprise plotting the minimum volume fraction value for every dose level across the DVHs of all of the generated fluence maps. Generating the upper bound DVH may comprise plotting the maximum volume fraction for every dose level across the DVHs of all of the generated fluence maps. Alternatively, or additionally, some methods may comprise interpolating dose distributions for additional fluence maps with treatment times between $T_{min}$ and $T_{max}$, calculating DVHs for these additional fluence maps, and generating upper and lower bound DVHs as described above. The bDVH may have a shaded region between the lower bound DVH and the upper bound DVH, which may help highlight the dose variability to the VOI that corresponds with the range of treatment times between $T_{min}$ and $T_{max}$.

In some variations, generating (310) additional fluence maps that have treatment delivery times between $T_{min}$ and $T_{max}$ may further comprise saving the set of fluence maps in a controller memory of the radiotherapy planning system. For example, the generated fluence maps (from steps 302, 306, and 310) may be stored in a database such that each fluence map is indexed by its treatment delivery time. Optionally, in addition to storing the set of fluence maps indexed by their treatment times, the database may also store the DVHs for each of the VOIs, dose coverage of each target region, mean dose for each OAR (or radiation-avoidance region) that correspond with each fluence map. This database may be used to facilitate the updating of the GUI as different treatment times are selected by the treatment time selector, as described further below.

Method (300) may optionally comprise updating (318) the variable DVH curve in the GUI to represent the dose delivered by a fluence map that has a treatment delivery time that approximates the treatment delivery time specified by the treatment time selector, and generating (320) a final fluence map based on a final selection of a treatment delivery time via the treatment time selector. Updating (318) the variable DVH curve to reflect the selection of different treatment delivery times reflected by user input via the treatment time selector may comprise referencing the database of fluence maps and/or DVHs by the selected treatment time to obtain and/or generate a fluence map that has a treatment delivery time that approximates the selected treatment delivery time. In some variations, the selected treatment delivery time may correspond to an entry in the database (i.e., a fluence map with the selected treatment delivery time has already been calculated, for example, in step 310) and the retrieved fluence map and/or DVHs may be used to update the variable DVH. In some variations, the selected treatment delivery time may not correspond to an entry in the database (i.e., a fluence map with the selected treatment delivery time has not been calculated), and updating the variable DVH may comprise generating an interpolated fluence map by interpolating between fluence maps that have treatment delivery times that bound the selected treatment delivery time and updating the variable DVH of the GUI based on the interpolated fluence map. For example, if the database has fluence maps and/or DVHs for treatment times 5 minutes and 7 minutes, and the selected treatment delivery time is 6 minutes, the method may comprise interpolating between the fluence map for treatment time 5 minutes and the fluence map for treatment time 7 minutes to update the variable DVH for treatment time 6 minutes. In variations where the database stores the DVHs for VOIs that correspond with a fluence map, the method may comprise interpolating between DVHs that have treatment delivery times that bound the selected treatment delivery time and updating the variable DVH of the GUI with the interpolated DVH. The generation of the final fluence map may occur after a user has tried different treatment times, evaluated the dose to one or more VOIs, and decided on the treatment time that is clinically practical and would provide a desired dose distribution to the various VOIs.

FIG. 4A depicts a flowchart representation of one variation of a method for generating (302) the first fluence map (i.e., fluence map having a treatment delivery time that may be used as the lower limit of a range of treatment times). Method (400) may comprise selecting or calculating (402) an estimated minimum treatment time, defining (404) a cost function having a plurality of penalty functions including a treatment time penalty function, where the weight of the treatment time penalty function is greater than the weight of the other penalty functions, and generating (406) a fluence map comprising a set of beamlet values by iteratively adjusting the beamlet values based on the cost function such that the fluence map delivers a prescribed dose to the target region. Calculating (402) an estimated minimum treatment time may comprise generating a fluence map that meets minimum dose criteria to the target region(s), without considering the irradiation of OARs, and calculating the time it would take a radiotherapy system to deliver the generated fluence map. In some variations, the calculation of the estimated minimum treatment time may use ideal radiotherapy system models (e.g., without unwanted artifacts). The defined cost function may also include OAR penalty functions, and in some variations where there is a high-priority OAR where the clinician deems it critical that the OAR is not over-irradiated, that OAR penalty function may have a heavier weight than the other OAR penalty functions (though still have a lower weight than the treatment time penalty function). In some variations, the treatment time penalty function may include a treatment time threshold that corresponds to the estimated minimum treatment time. During the iteration of beamlet values to generate the fluence map (406), an intermediate fluence map may be penalized for exceeding the treatment time threshold (i.e., exceeding the estimated minimum treatment time). This may differ from other treatment time penalty functions. For example, other treatment time penalty functions may be:

$$w \cdot T_{est}$$

Where w is a weight of the treatment time penalty function, and $T_{est}$ is the treatment time for a particular iteration of a fluence map. In contrast, a threshold-based treatment time penalty function may be:

$$w \cdot |T_{est} - T_{est\_minimum}|_1^+$$

Where $T_{est\_minimum}$ is the estimated minimum treatment time. Since the threshold-based treatment time penalty function is non-convex, some methods may comprise using a regularization algorithm, such as Moreau-Yosida regularization, to create a convex approximation of this penalty function. In some variations, generating (406) the fluence map may comprise iterating through beamlet values using any algorithm that solves convex optimization problems, such as a fast-iterative shrinkage-thresholding algorithm (FISTA).

FIG. 4B depicts a flowchart representation of one variation of a method for generating (306) the second fluence map (i.e., fluence map having a treatment delivery time that may be used as the upper limit of a range of treatment times). Method (410) may comprise defining (412) a cost function having a plurality of penalty functions including an organ-at-risk (OAR) penalty function and no treatment time penalty function, and generating (414) a fluence map comprising a set of beamlet values by iteratively adjusting the beamlet values based on the cost function such that the fluence map delivers a prescribed dose to the target region and plan quality metrics are within an acceptable range. One example of a plan quality metric is the mean dose to an OAR, and determining whether the plan quality metrics are within an acceptable range comprises determining whether changes of a mean dose to the OAR between iterations of the beamlet values is less than a selected threshold. The delivery time of the resultant fluence map may be used as the upper limit $T_{max}$ of the range of treatment times. In some variations, method (410) may optionally further comprise iterating on the set of beamlet values until the changes of a mean dose to an OAR between iterations starts to diverge or differ by more than a difference threshold. The delivery time of the fluence map at the iteration where the mean dose to the OAR differs by more than the difference threshold may be used as the upper limit $T_{max}$. In variations where there are multiple OARs, the plan quality metric may compare the mean doses (e.g., normalized mean doses) to the multiple OARs, and determining whether the plan quality metrics are within an acceptable range comprises determining whether changes of a mean dose to the multiple OARs between iterations of the beamlet values is less than the threshold for each OAR, i.e., difference in mean dose between iterations is less than a threshold. For example, the changes to the mean doses between iterations for all of the OARs may be less than one or more threshold values before stopping the iteration on the beamlet values. The mean dose difference threshold may be different for different OARs, e.g., the mean dose difference threshold for the heart may be different from the mean dose difference threshold for the spinal cord. Plan quality metrics may include dose values (e.g., normalized mean dose, maximum dose) to one or more OARs, and generating (414) the fluence map may comprise iterating on beamlet values until the dose values are within an acceptable range, i.e., the one or more OARs are not irradiated beyond acceptable levels. In some variations, plan quality metrics may comprise cost function values and the generating (414) the fluence map may comprise iterating on beamlet values until the cost function value is within an acceptable range of cost function values. Alternatively, plan quality metrics may comprise a dose-only cost function that includes only dose-based penalty functions, such as dose penalty functions for each of the OARs.

Methods for Generating Multiple Fluence Maps for Dynamic GUI Updates

In some variations, a method for generating a radiotherapy planning GUI that depicts radiation dose information in relation to various treatment delivery times may comprise generating multiple fluence maps before the GUI is output to a display device. For example, as described above, method (300) may comprise generating (310) additional fluence maps that have treatment delivery times within a range of treatment time (e.g., between $T_{min}$ and $T_{max}$). This set of fluence maps may be stored in a database and indexed by treatment delivery time. Optionally, the database may also contain the DVHs for each of the VOIs, dose coverage of each target region, mean dose for each OAR (or radiation-avoidance region) that correspond with each fluence map. The database may be stored in a controller memory of the radiotherapy planning system, and referenced to update the variable dose graphic (e.g., DVH) of one or more VOIs when a user is interacting with the GUI and selecting different treatment times. A method for generating fluence maps that have treatment delivery times that span a treatment time range (e.g., between $T_{min}$ and $T_{min}$) may comprise defining a cost function for each treatment time within the range that has a treatment time penalty function (e.g., a threshold-based treatment time penalty function), and iteratively adjusting initial fluence map beamlet values based on the defined cost function such that the target region receives the prescribed dose and changes of the cost function value between iterations is less than a selected threshold. The treatment delivery time for the resultant fluence map may be calculated and may be stored, along with the fluence map, in the database. In some variations, the initial fluence map beamlet values may be calculated based on previously-generated fluence maps that have treatment delivery times that are greater than and/or less than a particular treatment time. For example, as part of generating the bDVH for a GUI, the radiotherapy planning system may have generated the fluence map for the lower treatment time limit (e.g., the first fluence map in the method of FIG. 3) and the fluence map for upper treatment time limit (e.g., the second fluence map in the method of FIG. 3). The fluence maps for the lower and upper treatment time limits may be combined to provide an initial fluence map for a treatment time that is between the lower and upper limits (e.g., in the middle of the range of treatment times). For example, the initial fluence map may be a weighted combination of the fluence maps for the lower and upper treatment time limits, depending on how close the intermediate treatment time is to either the lower or upper treatment time limits. In some variations, the initial fluence map may be a Pareto optimal fluence map, e.g., a convex combination of the lower and upper limit fluence maps. An initial fluence map for an intermediate treatment time that is a combination of fluence maps having treatment delivery times that bound the intermediate treatment time (i.e., a lower treatment time that is less than the intermediate treatment time and a higher treatment time that is greater than the intermediate time) may provide an initial fluence map that converges more quickly (i.e., fewer optimization iterations) to a final set of beamlet values that optimizes (e g, minimizes) a cost function and/or meets dose objectives (e.g., plan quality metrics). In some variations, the initial fluence map may be a combination of two fluence maps that bound the intermediate treatment time, but in other variations, the initial fluence map may be combination of more than two fluence maps.

Some methods may comprise generating a database of fluence maps for a selected set of treatment times within the treatment time range. The fluence maps that are stored in the database may provide a meaningful sampling across the treatment time range. For example, a fluence map that has similar dose distribution characteristics (i.e., similar plan quality) as another fluence map in the database may not be added to the database, while a fluence map that has different dose distribution characteristics (i.e., different plan quality) as the fluence maps in the database may be added to the database. In some variations, all generated fluence maps, regardless of the similarity of their dose distribution characteristics (e.g., plan quality metric values) to other fluence maps in the database, may be added to the database. However, the treatment delivery times for fluence maps with similar dose distribution characteristics may define sub-ranges of treatment times for which no further fluence maps will be calculated. This selection criteria may help to populate the database with fluence maps that have treatment delivery times that span across the range of treatment times, which may help provide accurate approximations of dose distributions for fluences maps with different treatment delivery times.

In one variation, a method for generating a database of fluence maps for a selected set of treatment times within the treatment time range may comprise bisecting a range of treatment times (which has a lower limit and an upper limit), selecting the treatment time at the bisection point (i.e., at the midpoint or at the halfway point of the range of treatment times), generating a fluence map that has a treatment delivery time that approximates the treatment time at the bisection point, calculating a plan quality metric value for the generated fluence map, calculating a first difference between the plan quality metric value for the bisection treatment time and the corresponding plan quality metric value for the lower limit treatment time, and calculating a second difference between the plan quality metric value for the bisection treatment time and the corresponding plan quality metric value for the upper limit treatment time. The generated fluence map may be added to the set of fluence maps in a database stored in the treatment planning system controller. Alternatively, in some variations, the generated fluence map may be added to the set of fluence maps only if the first and/or second differences are greater than a specified margin. If the first and second differences are less than the specified margin, then the generated fluence map may not be added to the set of fluence maps. In some variations, generating the fluence map that has a treatment delivery time that approximates the bisection treatment time may comprise starting the beamlet value iterations with an intermediate fluence map that is a combination of the fluence maps having a treatment delivery time at the lower treatment time limit and the upper treatment time limit. These fluence maps may have been already calculated and stored into the database. The intermediate fluence map may provide a "warm start" to the beamlet value iteration process and help to reduce the number of iterations arriving (e.g., converging) at a final fluence map for the bisection treatment time. In some variations, the intermediate (i.e., "warm start") fluence map may be a Pareto optimal fluence map, and may be, for example, a convex combination of the fluence maps at the endpoints (e.g., lower and upper limits) of the treatment time range. While the variations described herein calculating ranges of treatment times using bisection, it should be understood that calculating ranges of treatment times may include dividing treatment time ranges at any desired time point within the range.

The bisection of the initial range of treatment times may create additional sub-ranges of treatment times, and adding fluence maps to the database may comprise repeatedly bisecting the sub-ranges of treatment times, generating fluence maps for the treatment times at each of the bisection treatment times, and determining whether the plan quality metric values for the generated fluence maps different from the plan quality metric values of the fluence maps that have already been included in the database. If the first and/or second differences are less than the specified margin, then the bisection treatment time may not be used as the end point for another sub-range of treatment times. However, if the first and/or second differences are greater than a specified margin, then the method may comprise defining new sub-ranges of treatment times using the bisection treatment time as an endpoint (e.g., as the lower limit of one new sub-range and as the upper limit of another new sub-range). For example, the initial range of treatment times may be defined by a lower limit $T_{min}$ and an upper limit $T_{max}$. As described above, a first fluence map that has a treatment delivery time of $T_{min}$ and a second fluence map that has a treatment delivery time of $T_{max}$ may be generated. These first and second fluence maps (and optionally, dose information for the one or more VOIs) may be included in the set of fluence maps and stored in the database. The method may then comprise bisecting the initial range by selecting a bisection treatment time (e.g., a midpoint in the range where the lower limit $T_{min}$ and an upper limit $T_{max}$ are endpoints):

$$T_{Bisection\_0} = \frac{(T_{max} - T_{min})}{2}$$

The method may then comprise calculating a fluence map that has a treatment delivery time of $T_{Bisection\_0}$ by generating an intermediate fluence map by combining the fluence maps that correspond to $T_{min}$ and $T_{max}$, and iterating on the beamlet values of the intermediate fluence map using a cost function that has a threshold-based treatment time penalty that sets $T_{Bisection\_0}$ as the treatment time threshold (using any of the methods described above). Generating the intermediate fluence map by combining the fluence maps that were already calculated for each of the endpoints may help reduce the computational complexity/load of calculating the fluence map for that midpoint by reducing the number of iterations (i.e., provide a "warm start") as compared to iterating on a fluence map that is derived without using the endpoint fluence maps. The resultant fluence map may have a treatment delivery time that approximates, or is equal to, $T_{Bisection\_0}$ The resultant fluence map that has a treatment time of $T_{Bisection\_0}$ may be added to the set of fluence maps and stored in the database. Then, a plan quality metric value may be calculated for the resultant fluence map (e.g., OAR dose exposure, etc.), and compared to the corresponding plan quality metric values of the first and second fluence maps. If the plan quality metric value differs from the plan quality metric values of the first and second fluence maps, then the method may then comprise bisecting the two sub-ranges that resulted from the first bisection. For example, the first sub-range would be from $T_{min}$ to $T_{Bisection\_0}$ and the next bisection treatment time would be:

$$T_{Bisection\_1} = \frac{(T_{Bisection\_0} - T_{min})}{2}$$

The second sub-range would be from $T_{Bisection\_0}$ to $T_{max}$ and the next bisection treatment time would be:

$$T_{Bisection\_2} = \frac{(T_{max} - T_{Bisection\_0})}{2}$$

The above steps (including the "warm start" generation of an intermediate fluence map for the beamlet value iterations) may be repeated for each of the new bisection treatment times $T_{Bisection\_1}$ and $T_{Bisection\_2}$, as well as their respective bisected sub-ranges. The method may comprise bisecting the sub-ranges of treatment timed until stopping conditions are met. For example, if the plan quality metric value for a fluence map that has a treatment delivery time bisection treatment time of a bisected treatment time sub-range does not differ sufficiently from the plan quality metric values of the fluence maps in the set of fluence maps (i.e., the difference is less than a specified margin), then the method may not include further bisections of that treatment time sub-range, e.g., the bisected sub-range defined by the bisection treatment time (e.g., between the lower limit of the bisected sub-range and the bisection treatment time) may not be further bisected. Alternatively, or additionally, a stopping condition may be when the treatment times selected by bisection are within a margin of the lower and upper limits of the sub-range, and/or when the plan quality metric value of the bisection treatment time fluence map is similar to (e.g., within a specified margin) of the plan quality metric values of the fluence maps in the database.

Optionally, for each fluence map added to the set of fluence maps stored in the database, some methods may comprise calculating DVHs for each VOI (e.g., target region, OAR, radiation-avoidance regions, etc.), and/or dose distribution information (e g, minimum dose, maximum dose, mean dose, dose coverage) for each target region, and storing this information in the database as linked to the fluence map that has a particular treatment delivery time.

FIG. 5 depicts one variation of a method for selecting treatment times within a range of treatment times and generating fluence maps that have treatment delivery times that correspond to (e.g., approximates) the selected treatment times that may be included in set of fluence maps that are stored in a database (e.g., a database of fluence maps for a selected set of treatment times within the treatment time range). Method (500) may be used, for example, as part of method (300) of FIG. 3 (e.g., step 310). The method may be repeated for multiple selected treatment times in recursively defined treatment time ranges. For example, the initial range of treatment times may have endpoints (lower and upper limits) $T_{min}$ and $T_{max}$, and the method may be recursively applied to sub-ranges within the initial range. The fluence maps and corresponding dose parameters, plan quality metric values, etc. for the endpoints of the initial range (or sub-range) may have already been generated as part of generating the dose graphics for the GUI or generated in a previous iteration of the method. In some variations, the sub-ranges may be successive bisections of the initial range. Method (500) may comprise selecting (502) a treatment time $t_{selected}$ between the endpoints of a range of treatment times, generating (504) an intermediate fluence map that approximates the Pareto optimal fluence map using a convex combination of the fluence maps that have the endpoint treatment times, generating (506) a fluence map for $t_{selected}$ by iterating on the beamlet values of the intermediate fluence map to find beamlet values that minimize a cost function that includes a threshold-based treatment time penalty function (where the threshold is $t_{selected}$) and penalty functions related to dose objective function(s), calculating (508) one or more of the treatment delivery time, dose to each VOI, DVH for each VOI, and the plan quality metric value for the fluence map generated for $t_{selected}$, storing (510) the generated fluence map for $t_{selected}$ and the above calculated quantities in a set of fluence maps, and calculating (512) a difference between the plan quality metric for $t_{selected}$ and the plan quality metric values for the endpoints. In some variations, if the plan quality metric difference is greater than a predetermined threshold, the generated fluence map may be added to the set of fluence maps, but if the plan quality metric difference is less than a predetermined threshold, the fluence maps and associated calculated quantities may not be stored in the database. The plan quality metric may comprise the mean dose(s) to one or more OARs (i.e., radiation-avoidance regions), as previously described. In some variations, the threshold-based treatment time penalty used to generate the fluence map for $t_{selected}$ may be the example described above. That is, the threshold-based treatment time penalty function may be:

$$w \cdot |T_{est} - t_{selected}|_1^+$$

Where $T_{est}$ is the treatment time for a particular iteration of a fluence map.

Method (500) may comprise defining (514) additional sub-ranges between the endpoints of the treatment time range and $t_{selected}$ if the plan quality metric difference is greater than a predetermined threshold, and repeatedly (516) selecting additional treatment times within the sub-ranges, generating fluence maps for each of the selected treatment times, storing the generated fluence maps, and defining additional sub-ranges if the plan quality values are sufficiently different from the endpoints and/or until stopping conditions are met. If the plan quality metric values of the fluence map generated for a particular treatment time are similar to the plan quality metric values of the treatment time range endpoint fluence maps (e.g., the plan quality metric difference is less than a predetermined threshold), then no sub-ranges may be further defined using the particular treatment time as an endpoint. Examples of stopping conditions may include when the next selected treatment time is close to either of the sub-range endpoints (e.g., when the next selected treatment time is within a specified margin of the endpoints) and when the plan quality metric value is sufficiently similar (e.g., within a specified margin) of the plan quality metric values of the fluence maps of the endpoints and/or the fluence maps that have been included in the database.

Method for Dynamic GUI Updates

The database of fluence maps generated using the methods described above may facilitate and support the rapid updating of the variable dose graphic of the GUI when a user selects different treatment times. If the fluence map corresponding to a treatment time selected by user is in the database, the dose information (including the DVH) may be retrieved and used to update the variable dose graphic. If the fluence map corresponding to a treatment time selected by user is not in the database, a method may comprise identifying the treatment times in the database that most closely bound the selected treatment time, and interpolating between the dose information for their corresponding fluence maps to update the GUI. For example, some methods may comprise identifying the treatment time in the database that is less than and closest to the selected treatment time, identifying the treatment time in the database that is greater than and closest to the selected treatment time, and interpolating between their dose information to derive the dose data for the selected treatment time.

Figure 6:
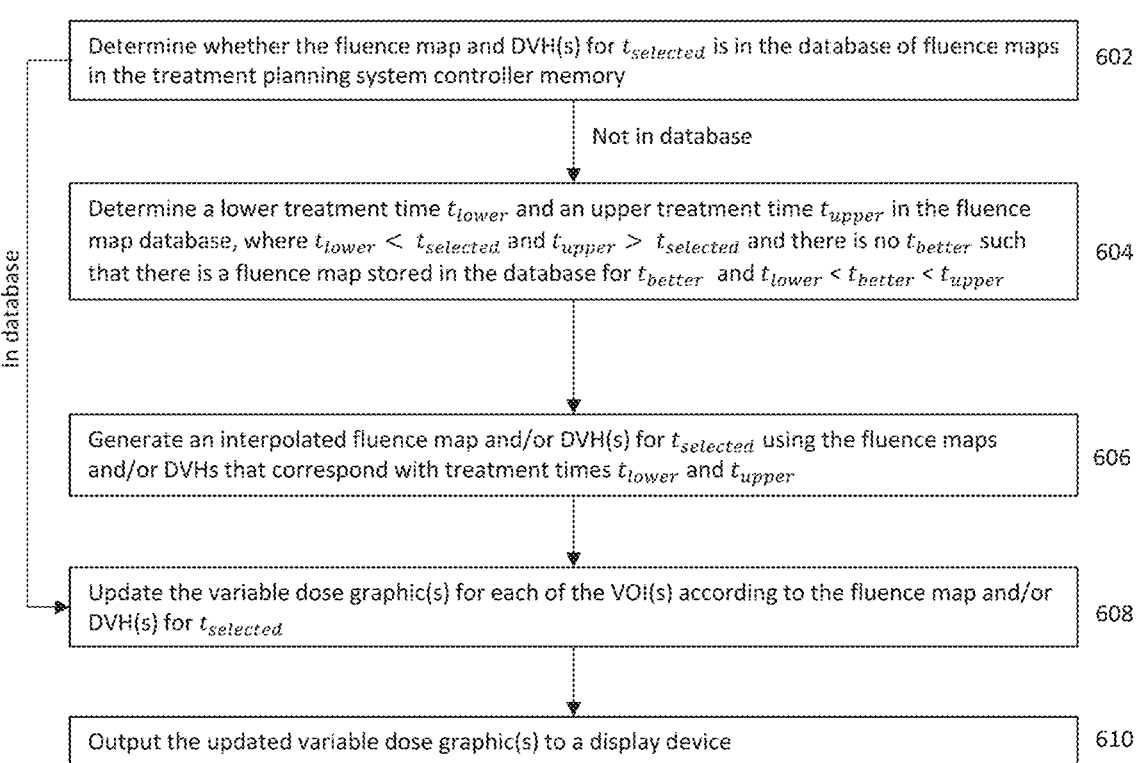
FIG. 6 depicts a flowchart representation of one variation of a method for updating the GUI based on a selection of a treatment time using the treatment time selector.

FIG. 6 depicts a flowchart representation of one method for updating the GUI using the database of fluence maps to update the GUI based on a selection of a treatment time $t_{selected}$ as indicated by the treatment time selector. Method (600) comprises determining (602) whether the fluence map and DVHs for $t_{selected}$ is in the database of fluence maps in the treatment planning system controller memory, and if the fluence and DVHs for $t_{selected}$ is not in the database, determining (604) a lower treatment time $t_{lower}$ and an upper treatment time $t_{upper}$ in the fluence map database, where $t_{lower} < t_{selected}$ and $t_{upper} > t_{selected}$ and there is no $t_{better}$ such that there is a fluence map stored in the database for $t_{better}$ and $t_{lower} < t_{better} < t_{upper}$, generating (606) an interpolated fluence map for $t_{selected}$ and/or DVH(s) using the fluence maps and/or DVHs that correspond with treatment times $t_{lower}$ and $t_{upper}$, updating (608) the variable dose graphic(s) for each of the VOI(s) according to the interpolated fluence map and/or DVH(s) for $t_{selected}$, and outputting (610) the updated variable dose graphic(s) to a display device. As described previously, the variable dose graphics may comprise DVHs to one or more VOIs, mean dose, and/or maximum dose to one or more VOIs. If it is determined (602) that the fluence map and DVH(s) for $t_{selected}$ is in the database of fluence maps, the method may comprise retrieving the fluence map and/or DVH(s) for the selected treatment time and using that data to update (608) the variable dose graphic. In cases where dose information for the selected treatment time is not in the database, the dose information may be generated (606) by interpolating between the dose information (e.g., DVHs) for the database entries having treatment times $t_{lower}$ and $t_{upper}$. Alternatively, or additionally, the fluence map may be generated (606) by interpolating between the fluence maps having treatment times $t_{lower}$ and $t_{upper}$, and then calculating the dose information from the interpolated fluence map. In some variations, the interpolation may be a linear interpolation.

Method of Generating a GUI Depicting the Treatment Time of a Fluence Map

FIG. 7 depicts a flowchart variation of a method for generating a GUI that comprises a plot of the initial treatment time (e.g., a fluence map with a particular cost function) relative to minimum and maximum treatment times. Method (700) comprises generating (702) a first fluence map that delivers a prescribed dose to a target region using a cost function having a plurality of penalty functions including a treatment time penalty function that is more heavily weighted than the other penalty functions, calculating (704) an amount of time $T_{min}$ for delivering the first fluence map, generating (706) a second fluence map that delivers a prescribed dose to a target region and optimizes an OAR dose metric, calculating (708) an amount of time $T_{max}$ for delivering the second fluence map, defining (710) a cost function having a plurality of penalty functions including a treatment time penalty function and OAR penalty function, where the weights of the penalty functions are user-specified, generating (712) a fluence map comprising a set of beamlet values by iteratively adjusting the beamlet values based on the cost function such that the fluence map delivers a prescribed dose to the target region, calculating (714) an amount of time $T_{delivery}$ to deliver the generated fluence map, generating (716) a GUI comprising a treatment time axis with a lower-limit indicator $T_{min}$, an upper-limit indicator at $T_{max}$, and a treatment time indicator at $T_{delivery}$, and outputting (718) the GUI to a display device. Generating (712) the fluence map may comprise using any of optimization algorithm, for example, FISTA. In some variations, method (700) may optionally comprise changing the cost function definition (710), re-generating the fluence map, calculating the treatment delivery time of the re-generated fluence map, and updating the GUI with the updated treatment delivery time. Changing the cost function may comprise adjusting the weights of the penalty functions that comprise the cost function and/or weights of any objective functions. This GUI may be used alone or in conjunction with any of the GUIs described herein (e.g., the GUI depicted in FIG. 1).

While the above methods and GUIs have been described in the context of depicting radiation dose information in relation to various treatment delivery times, similar methods may be used to depict radiation dose information in relation to other parameters or characteristics of radiation delivery. For example, the GUIs described herein may be used to depict radiation dose information in relation to the number of multi-leaf collimator (MLC) leaf transitions during a treatment session. That is, instead of calculating the treatment time associated with a fluence map, methods may calculate the number of MLC leaf transitions. A lower limit on MLC leaf transitions (e.g., $Leaf_{min}$) may be calculated from a fluence map generated using a cost function with an MLC leaf transition penalty function, and an upper limit on MLC leaf transitions (e.g., Leaf$_{max}$) may be calculated from a fluence map generated using a cost function without an MLC leaf transition penalty function. The DVHs for these fluence maps may be combined to calculate a bDVH that may be depicted on the GUI. The treatment time selector may be replaced with an MLC transition selector that selects for different numbers of MLC leaf transitions. The variable dose graphic may be a DVH (and/or other dose graphics such as text fields of mean dose, maximum dose, etc. to one or more VOIs) of a fluence map that is deliverable using the number of MLC leaf transitions indicated by the MLC transition selector. A GUI that dynamically updates the variable dose graphics based on user-selected changes in MLC leaf transitions may help generate a treatment plan that delivers a clinically acceptable dose to the patient while accounting for any limitations in the MLC.

While various inventive variations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive variations described herein. It is to be understood that the foregoing variations are presented by way of example only and that, within the scope of the appended claims and equivalents thereto, inventive variations may be practiced otherwise than as specifically described and claimed. The examples and variations of the present disclosure are directed to individual features, and/or methods described herein. In addition, any combination of two or more such features, and/or methods, if such features and/or methods are not mutually inconsistent, is included within the inventive scope of the present disclosure.

The above-described variations can be implemented in any of numerous ways. For example, embodiments of designing and making the technology disclosed herein may be implemented using hardware, software or a combination thereof. When implemented in software, the software code can be executed on any suitable processor or collection of processors, whether provided in a single computer (e.g., controller) or distributed among multiple computers (e.g., controllers).

Further, it should be appreciated that a radiotherapy treatment planning system may comprise a computer or controller that may be embodied in any of a number of forms, such as a rack-mounted computer, a desktop computer, a laptop computer, or a tablet computer. Additionally, a computer or controller may be embedded in a device not generally regarded as a computer but with suitable processing capabilities, including a Personal Digital Assistant (PDA), a smart phone or any other suitable portable or fixed electronic device.

Also, a computer or controller may have one or more input and output devices. These devices can be used, among other things, to present any of the GUIs described herein. Examples of output devices that can be used to interact with the GUIs described herein may include printers or display screens for visual presentation of output and speakers or other sound generating devices for audible presentation of output. Examples of input devices that can be used for a user interface include keyboards, and pointing devices, such as mice, touch pads (including touch displays), and digitizing tablets. As another example, a computer may receive input information through speech recognition or in other audible format.

Such computers or controllers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein (e.g., methods for generating a radiotherapy planning GUI that depicts radiation dose information in relation to various treatment delivery times, as disclosed above) may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more compact discs, optical discs, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The GUIs and methods of generating and updating the GUIs described herein may be performed using any type of computer code or set of computer-executable instructions that can be employed to program a computer or other processor to implement various aspects of examples as discussed above. Additionally, it should be appreciated that according to one aspect, the methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures, such as the fluence map and/or DVH databases described herein, may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which examples have been provided. The acts performed as part of the method may be ordered in any suitable way. Accordingly, variations may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one variation, to at least one, optionally including more than one, A, with no B present (and optionally including elements other than B); in another variation, to at least one, optionally including more than one, B, with no A present (and optionally including elements other than A); in yet another variation, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A graphical user interface for radiotherapy planning, the graphical user interface comprising:
   a bounded dose volume histogram (bDVH) for a target region comprising a lower bound DVH and an upper bound DVH that represent a range of radiation dose values to the target region over a range of treatment delivery times;
   a treatment time selector configured to receive user input that specifies a treatment delivery time within the range of treatment times; and
   a variable dose volume histogram (DVH) for the target region that represents a radiation dose to the target region that corresponds to the specified treatment delivery time,
   wherein the lower bound DVH corresponds to a lower-limit treatment delivery time value and the upper bound DVH corresponds to an upper-limit treatment delivery time value,
   wherein the lower-limit treatment delivery time value is a minimum treatment delivery time value, and the upper-limit treatment delivery time value is a maximum treatment delivery time value, and
   wherein the minimum treatment delivery time value is determined by
   generating a fluence map comprising a set of beamlet values by iteratively adjusting the beamlet values based on a cost function comprising a treatment time penalty function such that the fluence map delivers a prescribed dose to the target region and changes of a cost function value between iterations of the beamlet values is less than a selected threshold, and
   calculating an amount of time to deliver the generated fluence map.

2. A graphical user interface for radiotherapy planning, the graphical user interface comprising:
   a bounded dose volume histogram (bDVH) for a target region comprising a lower bound DVH and an upper bound DVH that represent a range of radiation dose values to the target region over a range of treatment delivery times;
   a treatment time selector configured to receive user input that specifies a treatment delivery time within the range of treatment times; and
   a variable dose volume histogram (DVH) for the target region that represents a radiation dose to the target region that corresponds to the specified treatment delivery time,
   wherein the lower bound DVH corresponds to a lower-limit treatment delivery time value and the upper bound DVH corresponds to an upper-limit treatment delivery time value, wherein the lower-limit treatment delivery time value is a minimum treatment delivery time value, and the upper-limit treatment delivery time value is a maximum treatment delivery time value, and
   wherein the maximum treatment delivery time value is determined by
   generating a fluence map comprising a set of beamlet values by iteratively adjusting the beamlet values based on a cost function comprising an organ-at-risk (OAR)

dose penalty function such that the fluence map delivers a prescribed dose to the target region and changes of a mean dose to the OAR between iterations of the beamlet values is less than a selected threshold, and calculating an amount of time to deliver the generated fluence map.

3. A graphical user interface for radiotherapy planning, the graphical user interface comprising:

a bounded dose volume histogram (bDVH) for a target region comprising a lower bound DVH and an upper bound DVH that represent a range of radiation dose values to the target region over a range of treatment delivery times;

a treatment time selector configured to receive user input that specifies a treatment delivery time within the range of treatment times;

a variable dose volume histogram (DVH) for the target region that represents a radiation dose to the target region that corresponds to the specified treatment delivery time;

a treatment time axis;

a lower limit indicator on the treatment time axis, wherein the lower-limit indicator is at a minimum treatment time in the range of treatment times;

an upper limit indicator on the treatment time axis, wherein the upper-limit indicator is at a maximum treatment time in the range of treatment times; and wherein the treatment time selector is located on the treatment time axis between the lower limit indicator and the upper limit indicator, wherein the treatment time indicator is at an initial treatment time for delivering a prescribed dose to the target region.

4. The graphical user interface of claim 3, wherein the initial treatment time is calculated by generating a fluence map comprising a set of radiation beamlet values by iteratively adjusting the beamlet values based on a cost function comprising an OAR penalty function such that the fluence map delivers the prescribed dose to the target region and changes of a cost function value between iterations of the beamlet values is less than a selected threshold; and calculating an amount of time to deliver the generated fluence map.

5. The graphical user interface of claim 3, wherein the minimum treatment time is determined by generating a fluence map comprising a set of beamlet values by iteratively adjusting the beamlet values based on a cost function comprising a treatment time penalty function such that the fluence map delivers the prescribed dose to the target region and changes of a cost function value between iterations of the beamlet values is less than a selected threshold, and calculating an amount of time it takes to deliver the generated fluence map.

6. The graphical user interface of claim 3, wherein the maximum treatment time is determined by generating a fluence map comprising a set of beamlet values by iteratively adjusting the beamlet values based on a cost function comprising an organ-at-risk (OAR) dose penalty function such that the fluence map delivers a prescribed dose to the target region and changes of a mean dose to the OAR between iterations of the beamlet values is less than a selected threshold, and calculating an amount of time to deliver the generated fluence map.

7. The graphical user interface of claim 3, wherein the lower bound DVH corresponds to a lower-limit treatment delivery time value and the upper bound DVH corresponds to an upper-limit treatment delivery time value.

8. The graphical user interface of claim 7, wherein the lower-limit treatment delivery time value is a minimum treatment delivery time value, and the upper-limit treatment delivery time value is a maximum treatment delivery time value.

9. The graphical user interface of claim 3, wherein the bDVH for the target region further comprises shading between the upper bound DVH curve and the lower bound DVH curve.

10. The graphical user interface of claim 3, wherein the variable DVH curve for the target region changes between the upper bound DVH curve and the lower bound DVH curve according to the user input to the treatment time selector.

11. The graphical user interface of claim 3, wherein the treatment time selector is a graphical slider that is movable between a first limit that corresponds to a low-threshold treatment delivery time value and a second limit that corresponds to a high-threshold treatment delivery time value, and wherein moving the slider to a position between the first and second limits corresponds to selecting the treatment delivery time.

12. The graphical user interface of claim 3, wherein the treatment time selector is a graphical dial that is rotatable between a first limit corresponding to a low-threshold treatment delivery time and a second limit corresponding to a high-threshold treatment delivery time, and wherein setting the dial to a position between the first and second limits corresponds to selecting the treatment delivery time.

13. The graphical user interface of claim 3, further comprising a second bDVH for a volume of interest (VOI) comprising a second lower bound DVH curve and a second upper bound DVH curve that represent a range of radiation dose values to the VOI over the range of treatment delivery times, and a second variable DVH curve for the VOI that represents a radiation dose to the VOI that corresponds to the specified treatment delivery time.

14. The graphical user interface of claim 13, wherein the second bDVH for the VOI further comprises shading between the upper bound DVH curve and the lower bound DVH curve.

15. The graphical user interface of claim 13, wherein the second variable DVH curve for the VOI changes between the upper bound DVH curve and the lower bound DVH curve of the second bDVH for the VOI according to the user input to the treatment time selector.

16. The graphical user interface of claim 13, wherein the VOI comprises a heart.

17. The graphical user interface of claim 13, wherein the VOI comprises a spinal cord.

18. The graphical user interface of claim 13, wherein the VOI comprises an esophagus.

19. The graphical user interface of claim 13, wherein the VOI comprises an organ-at-risk (OAR).

20. The graphical user interface of claim 13, further comprising a third bDVH for a second VOI comprising a third lower bound DVH curve and a third upper bound DVH curve that represent a range of radiation dose values to the second VOI over the range of treatment delivery times, and a third variable DVH curve for the second VOI that represents a radiation dose to the second VOI that corresponds to the specified treatment delivery time.

21. The graphical user interface of claim 20, further comprising a DVH-viewer selection menu that includes a graphical selection toggle for each of the first, second and third bDVHs, wherein a user-selection of a first toggle state displays the corresponding bDVH and a second toggle state hides the corresponding bDVH.

22. The graphical user interface of claim 21, wherein the first, second and third bDVHs are each depicted with different colors.

23. The graphical user interface of claim 3, further comprising a first text field that indicates a mean dose to the target region and a second text field that indicates a maximum dose to the target region for the specified treatment delivery time.

24. The graphical user interface of claim 3, further comprising a graphical indicator of the treatment delivery time specified by the treatment time selector.

25. The graphical user interface of claim 3, further comprising a command button that is triggers treatment plan optimization with the treatment delivery time specified by the treatment time selector.

\* \* \* \* \*